US010125373B2

(12) United States Patent
Mason et al.

(10) Patent No.: US 10,125,373 B2
(45) Date of Patent: Nov. 13, 2018

(54) GEMINIVIRAL VECTOR FOR EXPRESSION OF RITUXIMAB

(71) Applicants: THE ARIZONA BOARD OF REGENTS FOR AND ON BEHALF OF ARIZONA STATE UNIVERSITY, Tempe, AZ (US); Hugh Mason, Phoenix, AZ (US); Charles Arntzen, Gold Canyon, AZ (US); Sun Hee Rosenthal, Santa Ana, CA (US); Sean Winkle, Mesa, AZ (US); Andrew Diamos, Tempe, AZ (US)

(72) Inventors: Hugh Mason, Phoenix, AZ (US); Charles Arntzen, Gold Canyon, AZ (US); Sun Hee Rosenthal, Santa Ana, CA (US); Sean Winkle, Mesa, AZ (US); Andrew Diamos, Tempe, AZ (US)

(73) Assignee: Arizona Board of Regents on Behalf of Arizona State University, Tempe, AZ (US)

( * ) Notice: Subject to any disclaimer, the term of this patent is extended or adjusted under 35 U.S.C. 154(b) by 284 days.

(21) Appl. No.: 14/762,128

(22) PCT Filed: Jan. 22, 2014

(86) PCT No.: PCT/US2014/012575
§ 371 (c)(1),
(2) Date: Jul. 20, 2015

(87) PCT Pub. No.: WO2014/116721
PCT Pub. Date: Jul. 31, 2014

(65) Prior Publication Data

US 2015/0368660 A1 Dec. 24, 2015

Related U.S. Application Data

(60) Provisional application No. 61/755,256, filed on Jan. 22, 2013.

(51) Int. Cl.
*C12N 15/82* (2006.01)
*C07K 16/28* (2006.01)
*C12N 7/00* (2006.01)

(52) U.S. Cl.
CPC ...... *C12N 15/8258* (2013.01); *C07K 16/2887* (2013.01); *C12N 7/00* (2013.01); *C12N 15/8203* (2013.01); *C12N 15/8218* (2013.01); *C07K 2317/13* (2013.01); *C07K 2317/14* (2013.01); *C12N 2750/12043* (2013.01)

(58) Field of Classification Search
None
See application file for complete search history.

(56) References Cited

U.S. PATENT DOCUMENTS

| | | | |
|---|---|---|---|
| 3,817,837 | A | 6/1974 | Rubenstein et al. |
| 3,850,752 | A | 11/1974 | Schuurs et al. |
| 3,939,350 | A | 2/1976 | Kronick et al. |
| 3,996,345 | A | 12/1976 | Ullman et al. |
| 4,277,437 | A | 1/1981 | Maggio |
| 4,275,149 | A | 6/1981 | Litman et al. |
| 4,338,298 | A | 7/1982 | Myers |
| 4,366,241 | A | 12/1982 | Tom et al. |
| 4,659,774 | A | 4/1987 | Webb et al. |
| 4,682,195 | A | 7/1987 | Yilmaz |
| 4,683,195 | A | 7/1987 | Mullis et al. |
| 4,683,202 | A | 7/1987 | Mullis |
| 4,684,611 | A | 8/1987 | Schilperoort et al. |
| 4,748,018 | A | 5/1988 | Stolle et al. |
| 4,800,159 | A | 1/1989 | Mullis et al. |
| 4,816,571 | A | 3/1989 | Andrus et al. |
| 4,879,236 | A | 11/1989 | Smith et al. |
| 4,883,750 | A | 11/1989 | Whiteley et al. |
| 4,952,500 | A | 8/1990 | Finnerty et al. |
| 4,959,463 | A | 9/1990 | Froehler et al. |
| 5,141,813 | A | 8/1992 | Nelson |
| 5,264,566 | A | 11/1993 | Froehler et al. |
| 5,279,721 | A | 1/1994 | Schmid |

(Continued)

FOREIGN PATENT DOCUMENTS

| | | | |
|---|---|---|---|
| EP | 0266032 | A1 | 8/1987 |
| EP | 0329822 | A2 | 8/1988 |

(Continued)

OTHER PUBLICATIONS

Pujol et al. Fighting cancer with plant-expressed pharmaceuticals. (2007) Trends in Biotechnology; vol. 25; pp. 455-459.*
Zhao-Emonet et al., "Deletional and mutational analyses of the human CD4 gene promoter: characterization of a minimal tissue-specific promoter", Biochimica et Biophysica Acta, 1998, pp. 109-119, vol. 1442.
International Search Report and Written Opinion from related International Application No. PCT/US14/12575, dated Apr. 14, 2014, 12 pgs.
Kato et al., "Expression of Hepatitis B Virus Surface Antigen in Adult Rat Liver", The Journal of Biological Chemistry, 1991, pp. 3361-3364, vol. 266, No. 6.
Kay et al., "Duplication of CaMV 35S Promoter Sequences Creates a Strong Enhancer for Plant Genes", Science, 1987, pp. 1299-1302, vol. 236, No. 4806.

(Continued)

*Primary Examiner* — Cathy Kingdon Worley
(74) *Attorney, Agent, or Firm* — Polsinelli PC

(57) ABSTRACT

A single vector or multiple separate vectors that contain two or more non-competing replicons for transient expression of the heavy and light chains of Rituximab in *Nicotiana benthamiana* leaves is described. The correct assembly of these subunit proteins into functional oligomeric structures to optimize the expression is also described. This system advances plant transient expression technology by eliminating the need for non-competing viruses, and thus, enhances the realistic commercial application of the multi-replicon single vector system for producing Rituximab in plant cells.

7 Claims, 9 Drawing Sheets

Specification includes a Sequence Listing.

(56) References Cited

U.S. PATENT DOCUMENTS

| | | | |
|---|---|---|---|
| 5,302,523 | A | 4/1994 | Coffee et al. |
| 5,322,783 | A | 6/1994 | Tomes et al. |
| 5,384,253 | A | 1/1995 | Krzyzek et al. |
| 5,428,148 | A | 6/1995 | Reddy et al. |
| 5,464,765 | A | 11/1995 | Coffee et al. |
| 5,512,282 | A | 4/1996 | Krivan et al. |
| 5,538,877 | A | 7/1996 | Lundquist et al. |
| 5,538,880 | A | 7/1996 | Lundquist et al. |
| 5,548,066 | A | 8/1996 | Leneau et al. |
| 5,550,318 | A | 8/1996 | Adams et al. |
| 5,554,744 | A | 9/1996 | Bhongle et al. |
| 5,563,055 | A | 10/1996 | Townsend et al. |
| 5,574,146 | A | 11/1996 | Reddy et al. |
| 5,580,859 | A | 12/1996 | Felgner et al. |
| 5,589,466 | A | 12/1996 | Felgner et al. |
| 5,591,616 | A | 1/1997 | Hiei et al. |
| 5,602,244 | A | 2/1997 | Caruthers et al. |
| 5,610,042 | A | 3/1997 | Chang et al. |
| 5,645,897 | A | 7/1997 | Andra |
| 5,656,610 | A | 8/1997 | Shuler et al. |
| 5,702,932 | A | 12/1997 | Hoy et al. |
| 5,705,629 | A | 1/1998 | Bhongle |
| 5,736,524 | A | 4/1998 | Content et al. |
| 5,789,215 | A | 4/1998 | Berns et al. |
| 5,780,448 | A | 7/1998 | Davis |
| 5,840,873 | A | 11/1998 | Nelson et al. |
| 5,843,640 | A | 12/1998 | Patterson et al. |
| 5,843,650 | A | 12/1998 | Segev et al. |
| 5,843,651 | A | 12/1998 | Stimpson et al. |
| 5,843,663 | A | 12/1998 | Stanley et al. |
| 5,846,708 | A | 12/1998 | Hollis et al. |
| 5,846,709 | A | 12/1998 | Segev |
| 5,846,717 | A | 12/1998 | Brow et al. |
| 5,846,726 | A | 12/1998 | Nadeau et al. |
| 5,846,729 | A | 12/1998 | Wu et al. |
| 5,846,783 | A | 12/1998 | Wu et al. |
| 5,849,481 | A | 12/1998 | Urdea et al. |
| 5,849,486 | A | 12/1998 | Heller et al. |
| 5,849,487 | A | 12/1998 | Hase et al. |
| 5,849,497 | A | 12/1998 | Steinman |
| 5,849,546 | A | 12/1998 | Sousa et al. |
| 5,849,547 | A | 12/1998 | Cleuziat et al. |
| 5,851,772 | A | 12/1998 | Mirzabekov et al. |
| 5,853,990 | A | 12/1998 | Winger et al. |
| 5,853,992 | A | 12/1998 | Glazer et al. |
| 5,853,993 | A | 12/1998 | Dellinger et al. |
| 5,858,652 | A | 1/1999 | Laffler et al. |
| 5,861,244 | A | 1/1999 | Wang et al. |
| 5,863,732 | A | 1/1999 | Richards |
| 5,863,753 | A | 1/1999 | Haugland et al. |
| 5,866,331 | A | 2/1999 | Singer et al. |
| 5,866,366 | A | 2/1999 | Kallender |
| 5,871,986 | A | 2/1999 | Boyce |
| 5,900,481 | A | 4/1999 | Lough et al. |
| 5,856,092 | A | 5/1999 | Dale et al. |
| 5,905,024 | A | 5/1999 | Mirzabekov et al. |
| 5,910,407 | A | 6/1999 | Vogelstein et al. |
| 5,912,124 | A | 6/1999 | Kumar |
| 5,912,145 | A | 6/1999 | Stanley |
| 5,912,148 | A | 6/1999 | Eggerding |
| 5,916,776 | A | 6/1999 | Kumar |
| 5,916,779 | A | 6/1999 | Pearson et al. |
| 5,919,626 | A | 7/1999 | Shi et al. |
| 5,919,630 | A | 7/1999 | Nadeau et al. |
| 5,922,574 | A | 7/1999 | Minter |
| 5,925,517 | A | 7/1999 | Tyagi et al. |
| 5,925,565 | A | 7/1999 | Berlioz et al. |
| 5,928,862 | A | 7/1999 | Morrison |
| 5,928,869 | A | 7/1999 | Nadeau et al. |
| 5,928,905 | A | 7/1999 | Stemmer et al. |
| 5,928,906 | A | 7/1999 | Koster et al. |
| 5,929,227 | A | 7/1999 | Glazer et al. |
| 5,932,413 | A | 8/1999 | Celebuski |
| 5,932,451 | A | 8/1999 | Wang et al. |
| 5,935,791 | A | 8/1999 | Nadeau et al. |
| 5,935,819 | A | 8/1999 | Eichner et al. |
| 5,935,825 | A | 8/1999 | Nishimura et al. |
| 5,939,291 | A | 8/1999 | Loewy et al. |
| 5,942,391 | A | 8/1999 | Zhang et al. |
| 5,945,100 | A | 8/1999 | Fick |
| 5,994,624 | A | 11/1999 | Trolinder et al. |
| 5,981,274 | A | 12/1999 | Tyrrell et al. |
| 6,756,361 | B1 | 6/2004 | Fattom et al. |
| 6,770,278 | B1 | 8/2004 | Skelly |
| 6,936,258 | B1 | 8/2005 | Pavliak et al. |
| 2011/0262966 | A1 * | 10/2011 | Mason .............. C12N 15/8203 435/69.3 |

FOREIGN PATENT DOCUMENTS

| | | | |
|---|---|---|---|
| EP | 0320308 | A2 | 12/1988 |
| GB | 2202328 | A | 3/1988 |
| WO | 8706270 | A1 | 10/1987 |
| WO | 8810315 | A1 | 12/1988 |
| WO | 8906700 | A1 | 7/1989 |
| WO | 8909284 | A1 | 10/1989 |
| WO | 9409699 | A1 | 3/1994 |
| WO | 9506128 | A2 | 2/1995 |
| WO | 2010025285 | A1 | 3/2010 |
| WO | 2014116721 | A1 | 7/2014 |

OTHER PUBLICATIONS

Kochevenko et al., "Chimeric RNA/DNA Oligonucleotide-Based Site-Specific Modification of the Tobacco Acetolactate Syntase Gene", Plant Physiology, 2003, pp. 174-184, vol. 132.

Kraus et al., "Alternative promoter usage and tissue specific expression of the mouse somatostatin receptor 2 gene", FEBS Letters, 1998, pp. 165-170, vol. 428.

Kwoh et al., "Transcription-based amplification system and detection of amplified human immunodeficiency virus type 1 with a bead-based sandwich hybridization format", PNAS, 1989, pp. 1173-1177, vol. 86.

Lareyre et al., "A 5-Kilobase Pair Promoter Fragment of the Murine Epididymal Retinoic Acid-binding Protein Gene Drives the Tissue-specific, Cell-specific, and Androgen-regulated Expression of a Foreign Gene in the Epididymis of Transgenic Mice", The Journal of Biological Chemistry, 1999, pp. 8282-8290, vol. 274, No. 12.

Laufs et al "Geminivirus replication: Genetic and biochemical characterization of Rep protein function, a review", Biochimie, 1995, pp. 765-773, vol. 77.

Laufs et al., "In vitro cleavage and joining at the viral origin of replication by the replication initiator protein of tomato yellow leaf curl virus", PNAS, 1995, pp. 3879-3883, vol. 92.

Laufs et al., "Identification of the nicking tyrosine of geminivirus Rep protein", FEBS Letters, 1995, pp. 258-262, vol. 377.

Lazarowitz, "Geminiviruses: Genome Structure and Gene Function", Critical Reviews in Plant Sciences, 1992, pp. 327-349, vol. 11, No. 4.

Lee et al., "Tissue-Specific Promoter Usage in the D1A Dopamine Receptor Gene in Brain and Kidney", DNA and Cell Biology, 1997, pp. 1267-1275, vol. 16, No. 11.

Lee et al., "The Highly Basic Ribosomal Protein L41 Interacts with the β Subunit of Protein Kinase CKII and Stimulates Phosphorylation of DNA Topoisomerase IIα by CKII", Biochemical and Biophysical Research Communications, 1997, pp. 462-467, vol. 238, No. 2.

MacBeath et al., "Printing Proteins as Microarrays for High-Throughput Function Determination", Science, 2000, pp. 1760-1763, vol. 289.

Macejak et al., "Internal initiation of translation mediated by the 5' leader of a cellular mRNA", Naure, 1991, pp. 90-94, vol. 353.

Skolnick, "FDA Poster Campaign Targets Teen Smoking," Medical News & Perspective, 1997, 1 page, vol. 278, No. 8.

Mason et al., "Identification of a Methyl Jasmonate-Responsive Domain in the Soybean vspB Promoter", The Plant Cell, 1993, pp. 241-251, vol. 5.

Masuda et al., "Enhanced binding affinity for FcγRIIIa of fucose-negative antibody is sufficient to induce maximal antibody-dependent cellular cytotoxicity", Molecular Immunology, 2007, pp. 3122-3131, vol. 44.

(56) References Cited

OTHER PUBLICATIONS

Mernaugh et al., "An Overview of Phage-Displayed Recombinant Antibodies", Molecular Methods in Plant Pathology, Chapter 25, 1995, pp. 359-367.
Mor et al., "Geminivirus Vectors for High-Level Expression of Foreign Proteins in Plant Cells", Biotechnology and Bioengineering, 2003, pp. 430-437, vol. 81, No. 4.
Mori et al., "Non-fucosylated therapeutic antibodies: the next generation of therapeutic antibodies", Cytotechnology, 2007, pp. 109-114, vol. 55.
Nakamura et al., "Enzyme immunoassays: heterogeneous and homogeneous systems", Handbook of Experimental Immunology in Four Volumes, vol. 1: Immunochemistry, Chapter 27, pp. 27.1-27.20.
Nicolas et al., "Vectors: A Survey of Molecular Cloning Vectors and Their Uses," 1988, Chapter 25, pp. 493-513.
Nicolau et al., "Liposome-Mediated DNA Transfer in Eukaryotic Cells—Dependence of the Transfer Efficiency Upon the Type of Liposomes Used and the Host Cell Cycle Stage", Biochimica et Biophysica Acta, 1982, pp. 185-190, vol. 721.
Nicolau et al., "Liposomes as Carriers for in Vivo Gene Transfer and Expression", Methods in Enzymology, 1980, pp. 157-176, vol. 149.
Nomoto et al., "Cloning and characterization of the alternative promoter regions of the human LIMK2 gene responsible for alternative transcripts with tissue-specific expression", Gene, 1999, pp. 259-271, vol. 236.
Ohara et al., "One-sided polymerase chain reaction: The amplification of cDNA", PNAS, 1989, pp. 5673-5677, vol. 86.
Okuzaki et al., "Chimeric RNA/DNA oligonucleotide-directed gene targeting in rice", Plant Cell Rep, 2004, pp. 509-512, vol. 22.
Palmer et al., "The use of geminiviruses in biotechnology and plant molecular biology, with particular focus on Mastreviruses", Plant Science, 1997, pp. 115-130, vol. 129.
Palmer et al., "The Adult Rat Hippocampus Contains Primordial Neural Stem Cells", Molecular and Cellular Neuroscience, 1997, pp. 389-404, vol. 8.
Pandey et al., "Proteomics to study genes and genomes", Nature, 2000, pp. 837-846, vol. 405.
Pelletier et al., "Internal initiation of translation of eukaryotic mRNA directed by a sequence derived from poliovirus RNA", Nature, 1988, pp. 320-325, vol. 334.
Potrykus et al., "Molecular and general genetics of a hybrid foreign gene introduced into tobacco by direct gene transfer", Molecular & General Genetics, 1985, pp. 169-177, vol. 199, No. 2.
Ridgway, "Mammalian Expression Vectors", Biotechnology, 1988, Chapter 24, pp. 467-492, vol. 10.
Rippe et al., "DNA-Mediated Gene Transfer into Adult Rat Hepatocytes in Primary Culture", Molecular and Cellular Biology, 1990, pp. 689-695, vol. 10, No. 2.
Sambrook, Analysis of Genomic DNA by Southern Hybridization in Molecular Cloning: A Laboratory Manual 2nd edition, 1989, pp. 9.31-9.62, vol. 2.
Sambrook, "Protocol 3: Preparing Stocks of Bacteriophage by Plate Lysis and Elution," Molecular Cloning: A Laboratory Manual, 2001, pp. 2.34-2.37, Chapter 2.
Scholthof, "The Tombusvirus-encoded P19: from irrelevance to elegance", Microbiology, 2006, pp. 405-411, vol. 4.
Shinkawa et al., "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity", The Journal of Biological Chemistry, 2003, pp. 3466-3473, vol. 278, No. 5.
Strasser et al., "Generation of glyco-engineered Nicotiana benthamiana for the production of monoclonal antibodies with a homogeneous human-like N-glycan structure", Plant Biotechnology Journal, 2008, pp. 392-402 vol. 6.
Temin, "Retrovirus Vectors for Gene Transfer: Efficient Integration into and Expression of Exogenous DNA in Vertebrate Cell Genomes", Gene Transfer, Chapter 6,1986, pp. 149-188.
Tigges et al., "Human Herpes Simplex Virus (HSV)-Specific CD8+ CTL Clones Recognize HSV-2-Infected Fibroblasts after Treatment with IFN-γ or When Virion Host Shutoff Functions Are Disabled", The Journal of Immunology, 1996, pp. 3901-3910, vol. 156.
Timmermans et al., "Geminiviruses and Their Uses as Extrachromosomal Replicons", Annu. Rev. Plant Physiol. Plant Mol. Biol., 1994, pp. 79-112, vol. 45.
Tsumaki et al., "Modular Arrangement of Cartilage- and Neural Tissue-specific cis-Elements in the Mouse α2(XI) Collagen Promoter", The Journal of Biological Chemistry, 1998, pp. 22861-22864, vol. 273, No. 36.
Walker et al., "Isothermal in vitro amplification of DNA by a restriction enzyme/ DNA polymerase system", PNAS, 1992, pp. 392-396, vol. 89.
Weng et al., "Two Immunoglobulin G Fragment C Receptor Polymorphisms Independently Predict Response to Rituximab in Patients With Follicular Lymphoma", Journal of Clinical Oncology, 2003, pp. 3940-3947, vol. 21, No. 21.
Wong et al., "Appearance of β-lactamase activity in animal cells upon liposome-mediated gene transfer", Gene, 1980, pp. 87-94, vol. 10.
Wu et al,. "Promoter-Dependent Tissue-Specific Expressive Nature of Imprinting Gene, Insulin-like Growth Factor II, in Human Tissues", Biochemical and Biophysical Research Communications, 1997, pp. 221-226, vol. 233, No. 1.
Xiang et al., "A mini binary vector series for plant transformation", Plant Molecular Biology, 1999, pp. 711-717, vol. 40.
Zhang et al., "Bean Yellow Dwarf Virus Replicons for High-Level Transgene Expression in Transgenic Plants and Cell Cultures", Biotechnology and Bioengineering, 2006, pp. 271-279, vol. 93, No. 2.
Abbondanzo et al., "Prognostic significance of immunocytochemically determined pS2 in axillary node-negative brest carcinoma,", Breast Cancer Research and Treatment, 1990, vol. 16, pp. 1-182.
Allred et al., "Immunocytochemical Analysis of Estrogen Receptors in Human Breast Carcinomas—Evaluation of Cases and Review of the Literature Regarding Concordance with Biochemical Assay and Clinical Relevance," Bound Journals, 1990, vol. 125, No. 1, pp. 107-113.
Almendro et al., "Cloning of the Human Platelet Endothelial Cell Adhesion Molecule-1 Promoter and Its Tissue-Specific Expression Structural and Functional Characterization," The Journal of Immunology, 1996, vol. 157, pp. 5411-5421.
An et al., "Functional Analysis of the 3' Control Region of the Potato Wound-Inducible Proteinase Inhibitor II Gene," The Plant Cell, 1989, vol. 1, pp. 115-122.
Baichwal et al., "Vectors for gene transfer derived from DNA viruses: transient and stable expression of transferred genes," Gene Transfer, 1986, pp. 117-148.
Bellus, "How do Specialty Polymers Modify the Chemical and Pharmaceutical Industries?" Journal of Macromolecular Science, Part A, 1994, vol. A31, No. 10, pp. 1355-1376.
Brown et al., "Development and Evaluation of Monoclonal Antibody-Based Immunoassays: Breast Carcinoma-Associated Mucins as Tumor Markers," Immunology series, 1990, vol. 53, pp. 69-82.
Burke et al., "The Influence of Adjuvant on the Therapeutic Efficacy of a Recombinant Genital Herpes Vaccine," The Journal of Infectious Diseases, 1994, vol. 170, No. 5, pp. 1110-1119.
Capaldi et al., "Changes in Order of Migration of Polypeptides in Complex III and Cytochrome c Oxidase Under Different Conditions of SDS Polyacrylamide Gel Electrophoresis," Biochemicial and Biophysical Research Communications, 1977, vol. 74, No. 2, pp. 425-433.
Carbonelli et al., "A plasmid vector for isolation of strong promoters in *Escherichia coli*," FEMS Microbiology Letters, 1999, vol. 177, pp. 75-82.
Chandler et al., "RNA splicing specificity determined by the coordinated action of RNA recognition motifs in SR proteins," Proc. Natl. Acad. Sci. USA, 1997, vol. 94, pp. 3596-3601.
Chen et al., "High-Efficiency Transformation of Mammalian Cells by Plasmid DNA," Molecular and Cellular Biology, 1987, vol. 7, No. 8, pp. 2745-2752.
Chen et al., "Geminiviral vectors based on bean yellow dwarf virus for production of vaccine antigens and monoclonal antibodies in plants," Human Vaccines, 2011, vol. 7, No. 3, pp. 331-338.

(56) References Cited

OTHER PUBLICATIONS

Cocea et al., "Duplication of a Region in the Multiple Cloning Site of a Plasmid Vector to Enhance Cloning-Mediated Addition of Restriction Sites to a DNA Fragment," BioTechniques, 1997, vol. 23, pp. 814-816.
Coupar et al., "A general method for the construction of recombinant vaccinia viruses expressing multiple foreign genes," Gene, 1988, vol. 68, pp. 1-10.
Dall'Ozzo et al., "Rituximab-Dependent Cytotoxicity by Natural Killer Cells: Influence of FCGR3A Polymorphism on the Concentration-Effect Relationship," Cancer Research, 2004, vol. 64, pp. 4664-4669.
De Jager et al., "Current Status of Cancer Immunodetection with Radiolabeled Human Monoclonal Antibodies," Seminars in Nuclear Medicine, 1993, vol. XXIII, No. 2, pp. 165-179.
De Muynck et al., "Production of antibodies in plants: status after twenty years," Plant Biotechnology Journal, 2010, vol. 8, pp. 59-563.
Dietrich et al., "Fluorescent labelling reveals spatial separation of potyvirus populations in mixed infected *Nicotiana benthamiana* plants," Journal of General Virology, 2003, vol. 84, pp. 2871-2876.
Diveki et al.,"Limited utility of blue fluorescent protein (BFP) in monitoring plant virus movement," Biochimie, 2002, vol. 84, 997-1002.
Dong et al., "Oligonucleotide-directed gene repair in wheat using a transient plasmid gene repair assay system," Plant Cell Rep, 2006, vol. 25, pp. 457-465.
Doolittle et al., "Immunodetection of Lipoprotein Lipase: Antibody Production, Immunoprecipitation, and Western Blotting Techniques," Methods in molecular biology, 1999, vol. 109, pp. 1064-3745.
Fechheimer et al. "Transfection of mammalian cells with plasmid DNA by scrape loading and sonication loading," Proc. Natl. Acad. Sci. USA, 1987, vol. 84, pp. 8463-8467.
Fraley et al., "Entrapment of a bacterial plasmid in phospholipid vesicles Potential for gene transfer," Proc. Natl. Acad. Science USA, 1979, vol. 76, No. 7, pp. 3348-3352.
Friedmann, "Progress Toward Human Gene Therapy", Science, 1989, vol. 244, No. 4910, pp. 1275-1281.
Froehler et al., "Synthesis of DNA via deoxynucleoside H-phosphonate intermediates," Nucleic Acids Research, 1986, vol. 14, No. 13, pp. 5399-5407.
Frohman, "Race: Rapid Amplification of cDNA Ends," PCR Protocols: A Guide to Methods and Applications, 1990, pp. 28-38.
Garbarino et al., "Isolation of a ubiquitin-ribosomal protein gene (ubi3) from potato and expression of its promoter in transgenic plants," Plant Molecular Biology, 1994, vol. 24, pp. 119-127.
Giritch et al., "Rapid high-yield expression of full-size IgG antibodies in plants coinfected with noncompeting viral vectors," PNAS, 2006, vol. 103, No. 40, pp. 14701-14706.
Gopal, "Gene Transfer Method for Transient Gene Expression, Stable Transformation, and Cotransformation of Suspension Cell Cultures," Molecular and Cellular Biology, 1985, vol. 5, No. 5, pp. 1188-1190.
Graham et al., "A New Technique for the Assay of Infectivity of Human Adenovirus 5 DNA," Virology, 1973, vol. 52, pp. 456-467.
Grimsley et al., "Agrobacterium-mediated delivery of infectious maize streak virus into maize plants," Nature, 1987, vol. 325, pp. 177-179.
Gulbis et al., "Immunodetection of the p21-ras Products in Human Normal and Preneoplastic Tissues and Solid Tumors:", Progress in Pathology, 1993, vol. 24, No. 12, pp. 1271-1285.
Hanley-Bowdoin et al., "Expression of functional replication protein from tomato golden mosaic virus in transgenic tobacco plants," Proc. Natl. Acad. Science USA, 1990, vol. 87, pp. 1446-1450.
Hanley-Bowdoin et al., "Geminiviruses: Models for Plant DNA Replication, Transcription, and Cell Cycle Regulations," Critical Review in Plant Sciences, 1999 vol. 18, No. 1, pp. 71-106.
Harland et al., "Translation of mRNA Injected into Xenopus Oocytes is Specifically Inhibited by Antisense RNA," The Journal of Cell Biology, 1985, vol. 101, pp. 1094-1099.
Hayes et al., "Gene amplification and expression in plants by a replicating geminivirus vector," Nature, 1988, vol. 334, pp. 179-182.
Hermonat et al., "Use of adeno-associated virus as a mammalian DNA cloning vector: Transduction of neomycin resistance into mammalian tissue culture cells," Proc. Natl. Acad. Science USA, 1984, vol. 81, pp. 6466-6470.
Horwich et al., "Synthesis of Hepadnavirus Particles That Contain Replication-Defective Duck Hepatitis B Virus Genomes in Cultured HuH7 Cells," Journal of Virology, 1990, vol. 64, No. 2, pp. 642-650.
Huang et al., "A DNA Replicon System for Rapid High-Level Production of Virus-Like Particles in Plants," Biotechnology and Bioengineering, 2009, vol. 103, pp. 706-714.
Huang et al., "High-Level Rapid Production of Full-Size Monoclonal Antibodies in Plants by a Single-Vector DNA Replicon System," Biotechnology and Bioengineering, 2010, vol. 106, No. 1 pp. 9-17.
Hull et al., "Electron Microscopy on the Behavior of Two Strains of Alfalfa Mosaic Virus ini Mixed Infections," Virology, 1970, vol. 42, pp. 773-776.
Huston et al., "Protein Engineering of Single-Chain Fv Analogs and Fusion Proteins," Methods in Enzymology, 1991, vol. 203, pp. 46-88.
Innis et al., "DNA sequencing with Thermus aquaticus DNA polymerase and direct sequencing of polymerase chain reaction-amplified DNA," Proc. Natl. Acad. Science USA, 1988, vol. 85, pp. 9436-9440.
Inouye et al., "Up-promoter mutations in the Ipp gene of *Escherichia coli*," Nucleic Acids Research, 1985, vol. 13, No. 9, pp. 3101-3110.
Jefferson, "Assaying Chimeric Genes in Plants: The GUS Gene Fusion System," Plant Molecular Biology Reporter, 1987, vol. 5, No. 4, pp. 387-405.
Johnson et al., "Construction of Single-Chain Fv Derivatives of Monoclonal Antibodies and Their Production in *Escherichia coli*," Methods in Enzymology, 1991, vol. 203, 88-98.
Kaeppler et al. "Silicon carbide fiber-mediated DNA delivery into plant cells," Plant Cell Reports, 1990, vol. 9, pp. 415-418.
Kaneda et al., "Introduction and Expression of the Human Insulin Gene in Adult Rat Liver," The Journal of Biological Chemistry, 1989, vol. 264, No. 21, pp. 12126-12129.
Kanevski et al., "Tobacco lines with high copy number of replicating recombinant geminivirus vectors after bioloistic DNA delivery," The Plant Journal, 1992, vol. 2, No. 4, pp. 457-463.

* cited by examiner

GEMINIVIRAL VECTOR FOR EXPRESSION OF RITUXIMAB

CROSS-REFERENCE

This disclosure claims priority to U.S. provisional application Ser. No. 61/755,256, filed on Jan. 22, 2013 and entitled "Geminiviral Vector For Expression Of Rituximab," which is incorporated herein by reference in its entirety.

STATEMENT REGARDING FEDERALLY SPONSORED RESEARCH

This invention was made with government support under Grant Numbers AI066332, AI062150 and AI061253 awarded by the National Institutes of Health. The government has certain rights in the invention.

FIELD OF THE INVENTION

The present invention relates generally to the fields of genetic engineering of plants. In particular, the invention relates to the transformation of plants using recombinant DNA techniques to express Rituximab.

BACKGROUND OF THE INVENTION

Production of monoclonal antibodies (mAb's) in plants has developed greatly over the past two decades. The yields of recombinant proteins produced in plants are generally much lower than those routinely achieved in other systems. High-level production of functional multiplex proteins in plant is not a routine matter, sometimes it is quite challenging. Techniques to optimize heterologous protein overproduction in plants have been explored for host strain selection, plasmid copy numbers, transcription level, promoter selection, mRNA stability, and codon usage, all of which affect the yields of the foreign proteins differently from construct to construct, and from plant species to plant species. When a viral replicon, such as a geminiviral vector, is utilized in order to enhance expression, the performance of the system can be affected by the linear arrangement of DNA elements in the replicon structure, plant developmental stage, or environmental factors, all of which may affect replicon amplification and thereby, protein expression. Oftentimes, the recombinant protein itself plays an important role in determining the yield because some proteins are inherently less stable than others, and some proteins produce unanticipated negative effects on plant growth. In addition, the presence of a signal peptide, the presence of chaperones or protease activity, coexpression of a corresponding antigen, or a stabilizing protein partner, can significantly affect the yield of recombinant protein in plant cells.

Rituximab is a genetically engineered chimeric monoclonal antibody (mAb) anti-CD20 IgG1 licensed in 1997 for treatment of non-Hodgkins lymphoma, under the name Rituxan (Marwick, 1997). Originally isolated as a mouse mAb, the chimeric version replaced most of the mouse-specific regions with human sequences, in order to avoid immune responses in humans. Clinical data from genetic analyses of leukocyte receptor (FcγR) polymorphisms in cancer patients treated with Rituximab showed that antibody-dependent cellular cytotoxicity (ADCC) is a critical mechanism for its clinical efficacy (Weng et al., 2003; Dall'Ozzo et al., 2004). Rituximab-based ADCC is mediated by natural killer (NK) cells that bind the mAb Fc via FcγRIIIa (Dall'Ozzo et al, 2004).

Plants are attractive as pharmaceutical protein factories because they potentially can produce large volumes of products efficiently and sustainably and, under certain conditions, can have significant advantages in manufacturing costs. The unique nicking function of the Rep protein of geminiviruses (Laufs et al, 1995a; Laufs et al, 1995b) allows for replicative release of recombinant viral DNA cloned between a tandem repeat of the LIR from a chromosome-integrated site (Hayes et al, 1988; Grimsley et al, 1987; Kanevski et al, 1992). A previous study has indeed shown that an earlier version, the Bean Yellow Dwarf Virus derived vector and co-expressed with Rep driven by an inducible promoter in stable transgenic potato, produced an 80-fold increase in mRNA and a 10-fold increase in transgenic protein expression (Zhang and Mason, 2006). In order to scale up the productivity of Rituximab in plant, optimization of Rituximab expression in *N. benthamiana* for plant-produced mAb's with enhanced efficacy is therefore needed. The utilization of advanced and optimized replicon vectors in transient transgenic technologies was explored herein to allow a rapid assessment of pharmaceutical candidates and a scalable platform for commercial production.

SUMMARY OF THE INVENTION

Among the various aspects of the present invention, the present invention relates to a vector system comprising: (1) a first nucleic acid segment comprising at least one promoter, a 5'UTR, a region encoding a first part of a product of interest, a 3' terminator, and a short intergenic region (SIR) of a geminivirus genome, wherein the first nucleic acid segment is flanked on either side by a long intergenic region (LIR) of a geminivirus genome; (2) a second nucleic acid segment comprising at least one promoter, a 5'UTR, a region encoding a second part of a product of interest, a 3' terminator, and a short intergenic region (SIR) of a geminivirus genome, wherein the second nucleic acid segment is flanked on either side by a long intergenic region (LIR) of a geminivirus genome; and (3) one or more nucleic acid segment that comprises nucleic acids encoding Rep and RepA proteins of a geminivirus genome; wherein the first nucleic acid segment and the second nucleic acid segment are separate replicons and are non-competing; and wherein the vector system expresses the first and the second chain of Rituximab at a high level. In one embodiment of the vector system, the first nucleic acid segment and the second nucleic acid segment are comprised in a single vector. In another embodiment of the vector system, the first nucleic acid segment and the second nucleic acid segment are comprised in separate vectors. In yet another embodiment, the one or more nucleic acid segment that comprises nucleic acids encoding Rep and RepA proteins of a geminivirus genome is comprised in a vector without the first or the second nucleic acid segment. In still another embodiment, the one or more nucleic acid segment that comprises nucleic acids encoding Rep and RepA proteins of a geminivirus genome is comprised in a vector comprising either the first, or the second, or both the first and the second nucleic acid segment. In some embodiments, the Rep and RepA encoding nucleic acids have a typical native viral relative expression. In some other embodiments, the Rep and RepA encoding nucleic acids have an atypical relative expression. In yet some other embodiments, the vector system may further comprise a nucleic acid segment that comprises a gene-silencing inhibitor. In one embodiment of the vector system, the 5'UTR and the 3' terminator of the first nucleic acid segment are same as the 5'UTR and the 3' terminator of the second nucleic acid segment. Alternatively, in some embodiment, the 5'UTR and the 3' terminator of the first nucleic acid segment different from the 5'UTR and the 3' terminator of the second nucleic acid segment.

Another aspect of the present invention provides a vector system comprising: (1) a first nucleic acid segment comprising at least one promoter, a 5'UTR, a region encoding a first chain of Rituximab, and a 3' terminator, and a short intergenic region (SIR) of a geminivirus genome, wherein the first nucleic acid segment is flanked on either side by a long intergenic region (LIR) of a geminivirus genome; (2) a second nucleic acid segment comprising at least one promoter, a 5'UTR, a region encoding a second chain of Rituximab, a 3' terminator, and a short intergenic region (SIR) of a geminivirus genome, wherein the second nucleic acid segment is flanked on either side by a long intergenic region (LIR) of a geminivirus genome; and (3) one or more nucleic acid segment that comprises a nucleic acid encoding Rep and RepA proteins of a geminivirus genome; wherein the first nucleic acid segment and the second nucleic acid segment are separate replicons in different vectors, as such the first nucleic acid segment is in a first vector and the second nucleic acid segment is in a second vector, and two replicons are non-competing; wherein the 5'UTR of the first nucleic acid segment is the same as the 5'UTR of the second nucleic acid segment; wherein the 3' terminator of the first nucleic acid segment is the same as the 3' terminator of the second nucleic acid segment, and wherein the vector system expresses the first and the second chain of Rituximab at a high level. In one embodiment, the one or more nucleic acid segment comprising a nucleic acid encoding Rep and RepA proteins of a geminivirus genome is comprised in both the first and the second vectors. In another embodiment, the one or more nucleic acid segment comprising a nucleic acid encoding Rep and RepA proteins of a geminivirus genome is comprised in a separate third vector.

Still another aspect of the present invention provides a vector system comprising: (1) a first nucleic acid segment comprising at least one promoter, a 5'UTR, a region encoding a first chain of Rituximab, and a 3' terminator, and a short intergenic region (SIR) of a geminivirus genome, wherein the first nucleic acid segment is flanked on either side by a long intergenic region (LIR) of a geminivirus genome; (2) a second nucleic acid segment comprising at least one promoter, a 5'UTR, a region encoding a second chain of Rituximab, a 3' terminator, and a short intergenic region (SIR) of a geminivirus genome, wherein the second nucleic acid segment is flanked on either side by a long intergenic region (LIR) of a geminivirus genome; and (3) one or more nucleic acid segment that comprises a nucleic acid encoding Rep and RepA proteins of a geminivirus genome; wherein the first nucleic acid segment and the second nucleic acid segment are separate replicons in a single vector, as such both the first nucleic acid segment and the second nucleic acid segment are in one vector, and two replicons are non-competing; wherein the 5'UTR of the first nucleic acid segment is the same as the 5'UTR of the second nucleic acid segment; wherein the 3' terminator of the first nucleic acid segment is the same as the 3' terminator of the second nucleic acid segment, and wherein the vector system expresses the first and the second chain of Rituximab at a high level.

Yet another aspect of the present invention provides a method of producing Rituximab in a plant cell, which comprises: (1) obtaining a vector system comprising: (a) a first nucleic acid segment comprising at least one promoter, a 5'UTR, a region encoding a first chain of Rituximab, a 3' terminator, and a short intergenic region (SIR) of a geminivirus genome wherein the first nucleic acid segment is flanked on either side by a long intergenic region (LIR) of a geminivirus genome; (b) a second nucleic acid segment comprising at least one promoter, a 5'UTR, a region encoding a second chain of Rituximab, a 3' terminator, and a short intergenic region (SIR) of a geminivirus genome, wherein the second nucleic acid segment is flanked on either side by a long intergenic region (LIR) of a geminivirus genome; and (c) one or more nucleic acid segment that comprises nucleic acids encoding Rep and RepA proteins of a geminivirus genome; wherein the first nucleic acid segment and the second nucleic acid segment are separate replicons and are non-competing; and wherein the vector system expresses the first and the second chain of Rituximab at a high level; (2) introducing the vector system into a plant cell; and (3) allowing independent and non-competing amplification and expression of the replicons comprising the first and the second chain of Rituximab. In the step (3) of this general method, a full assembly of the first and the second chains of Rituximab may follow the independent and non-competing amplification and expression of the replicons. In one embodiment, the first and the second nucleic acid segment are in separate vectors, as such the first nucleic acid segment is in the first vector and the second nucleic acid segment is in the second vector. One exemplary first vector is pBYR9-MRtxG, as depicted in FIG. 2A, and one exemplary second vector is pBYR9-MRtxK, as depicted in FIG. 2B. In another embodiment, the first and the second nucleic acid segment are in a single vector, as such the single vector has multiple replicons. One exemplary single vector is pBYR29a-MRtx, as depicted in FIG. 2E.

Other aspects and features of the disclosure are described more thoroughly below.

(A) pBYR27b, a dual replicon geminiviral vector for co-expression of IgG heavy and light chains. One coding sequence is to be inserted between XbaI and SacI or XbaI and SmaI, which occur in a multi-cloning sequence (mcs) and another coding sequence is to be inserted between BsrGI and KpnI. T-DNA left (LB) and right (RB) borders demarcate the boundaries of the DNA that is transferred into plant cells by *Agrobacterium tumefaciens;*

Figure 1:
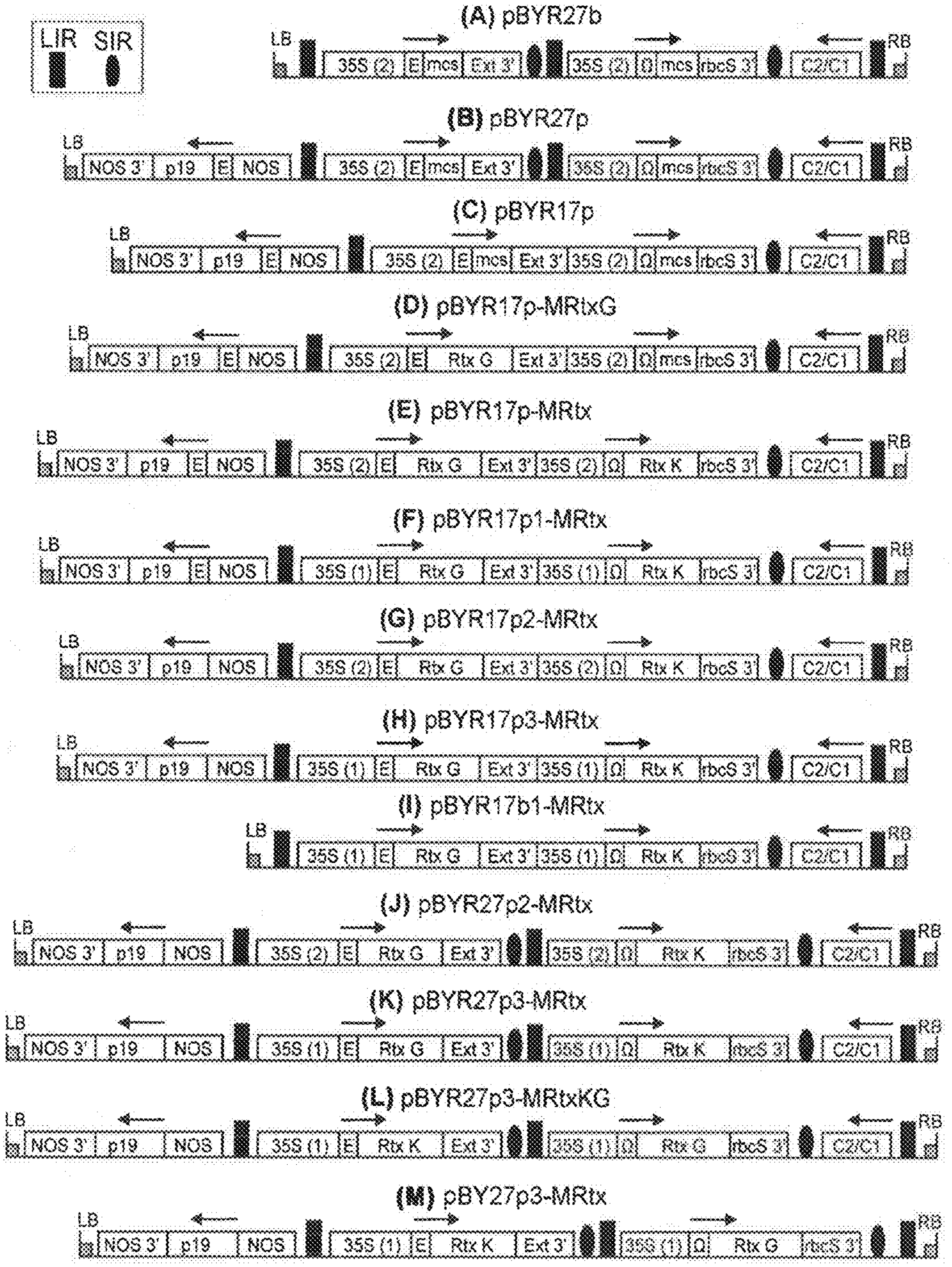
FIG. 1 depicts construct maps for a set of vectors. Label description: LIR, long intergenic region of BeYDV; SIR, short intergenic region of BeYDV; C2/C1, complementary sense coding regions of BeYDV encoding the viral Rep and RepA proteins; 35S (2), promoter of 35S RNA from cauliflower mosaic virus having duplicated enhancer region; mcs, multiple cloning site; E, tobacco etch virus 5' UTR; Ext 3', tobacco extensin 3' UTR and polyadenylation signal; Ω, tobacco mosaic virus 5' UTR; rbcS 3', pea Rubisco small subunit 3' UTR and polyadenylation signal; NOS, nopaline synthase promoter from *A. tumefaciens*; p19, coding sequence of RNAi gene silencing inhibitor from tomato bushy stunt virus; NOS 3', nopaline synthase 3' UTR and polyadenylation signal. The vectors are.

(B) pBYR27p, a dual replicon geminiviral vector for co-expression of IgG heavy and light chains. pBYR27p was constructed by insertion of an expression cassette for p19 between the T-DNA left border and the geminiviral LIR of pBYR27b (FIG. 1A);

(C) pBYR17p, a single replicon geminiviral vector for co-expression of IgG heavy and light chains. The LIR and SIR elements that lie between the EcoRI site at 3' end of Ext 3' and PstI site at 5' end of P 35S×2e in pBYR27p (FIG. 1B) were deleted by fusion of the EcoRI and PstI sites;

(D) pBYR17p-MRtxG, a single replicon geminiviral vector for co-expression of Rituximab heavy chain. The Rituximab heavy chain (Rtx G) coding sequence is inserted at XbaI and SacI;

(E) pBYR17p-MRtx, a single replicon geminiviral vector for co-expression of Rituximab heavy and light chains, with the Rituximab heavy chain (Rtx G) coding sequence inserted at XbaI and SacI and the light chain (Rtx K) inserted at BsrGI and KpnI;

(F) pBYR17p1-MRtx, a single replicon geminiviral vector for co-expression of Rituximab heavy and light chains. pBYR17p1-MRtx is similar to pBYR17p-MRtx (FIG. 1E), except that the 35S promoters [35S (1)] driving expression of the heavy and light chains have single instead of double enhancer regions;

(G) pBYR17p2-MRtx, a single replicon geminiviral vector for co-expression of Rituximab heavy and light chains. pBYR17p2-MRtx is similar to pBYR17p-MRtx (FIG. 1E), except that p19 expression cassette does not contain the TEV 5' UTR;

(H) pBYR17p3-MRtx, a single replicon geminiviral vector for co-expression of Rituximab heavy and light chains. pBYR17p3-MRtx is similar to pBYR17p2-MRtx (FIG. 1G), except that the 35S promoters [35S (1)] driving expression of the heavy and light chains have single instead of double enhancer regions;

(I) pBYR17b1-MRtx, a single replicon geminiviral vector for co-expression of Rituximab heavy and light chains. pBYR17b1-MRtx is similar to pBYR17p3-MRtx (FIG. 1H), except that it does not contain an expression cassette for p19;

(J) pBYR27p2-MRtx, a dual replicon geminiviral vector for co-expression of Rituximab heavy and light chains. This vector generates a separate replicon for heavy and light chains. The 35S promoters [35S (2)] contain duplicated enhancers;

(K) pBYR27p3-MRtx, a dual replicon geminiviral vector for co-expression of Rituximab heavy and light chains. pBYR27p3-MRtx is similar to pBYR27p2-MRtx (FIG. 1J) except that the 35S promoters [35S (1)] contain single rather than duplicated enhancers;

(L) pBYR27p3-MRtxKG, a dual replicon geminiviral vector for co-expression of Rituximab heavy and light chains. pBYR27p3-MRtxKG is similar to pBYR27p3-MRtx (FIG. 1K) except that heavy (Rtx G) and light (Rtx K) chain coding sequences have switched positions;

(M) pBY27p3-MRtx, a dual replicon geminiviral vector for co-expression of Rituximab heavy and light chains. pBY27p3-MRtx is similar to pBYR27p3-MRtx (FIG. 1K) except that the C2/C1 gene for expression of Rep/RepA is deleted.

Figure 2:
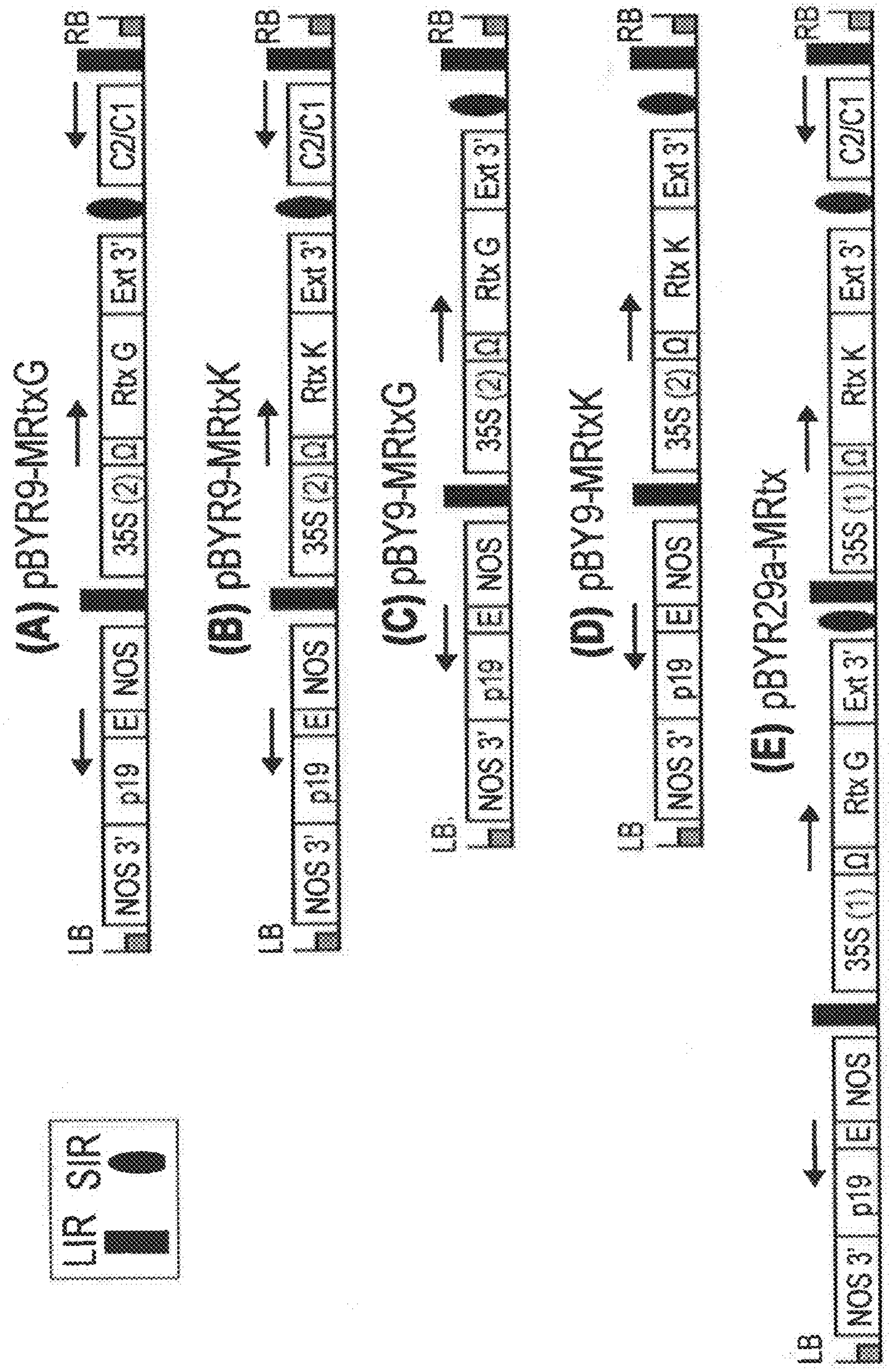

FIG. 2 construct maps for another set of vectors. The label description is the same as those in FIG. 1. The vectors are:

(A) pBYR9-MRtxG, a single replicon geminiviral vector for expression of Rituximab heavy chain. Labeling of components is as in FIG. 1J;

(B) pBYR9-MRtxK, a single replicon geminiviral vector for expression of Rituximab light chain. Labeling of components is as in FIG. 2A;

(C) pBY9-MRtxG, a single replicon geminiviral vector for expression of Rituximab heavy chain. pBY9-MRtxG is similar to pBYR9-MRtxG (FIG. 2A) except that the C2/C1 gene for expression of Rep/RepA is deleted;

(D) pBY9-MRtxK, a single replicon geminiviral vector for expression of Rituximab light chain. pBY9-MRtxK is similar to pBYR9-MRtxK (FIG. 2B) except that the C2/C1 gene for expression of Rep/RepA is deleted;

(E) pBYR29a-MRtx, a dual replicon geminiviral vector for co-expression of Rituximab heavy and light chains. pBYR29a-MRtx is similar to pBYR27p3-MRtx (FIG. 1K) except that both heavy and light chain cassettes use the TMV 5'UTR (Ω) and extensin 3' terminator (Ext 3'), and the p19 expression cassette contains the TEV 5'UTR (E).

Figure 3:
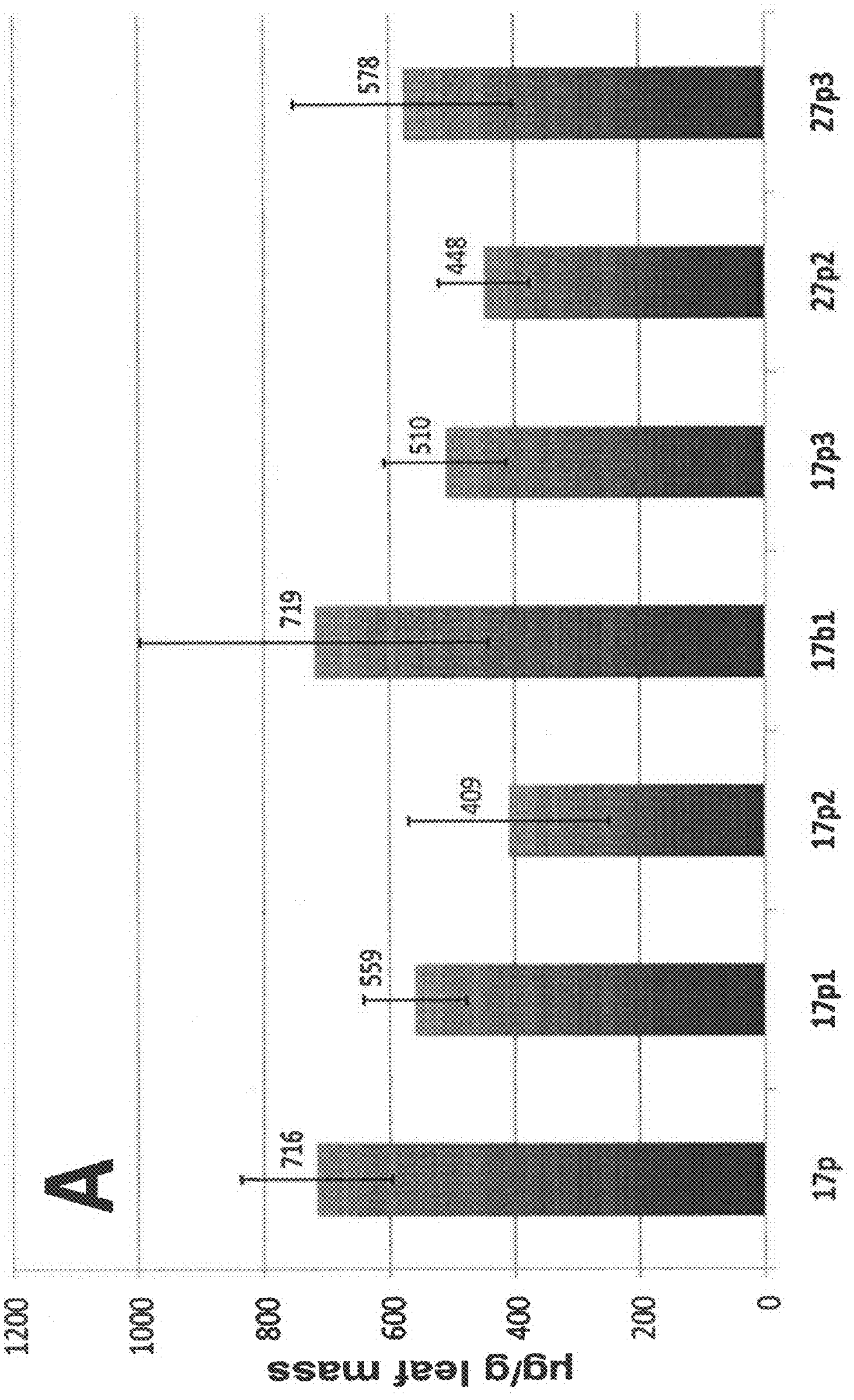
Figure 3:
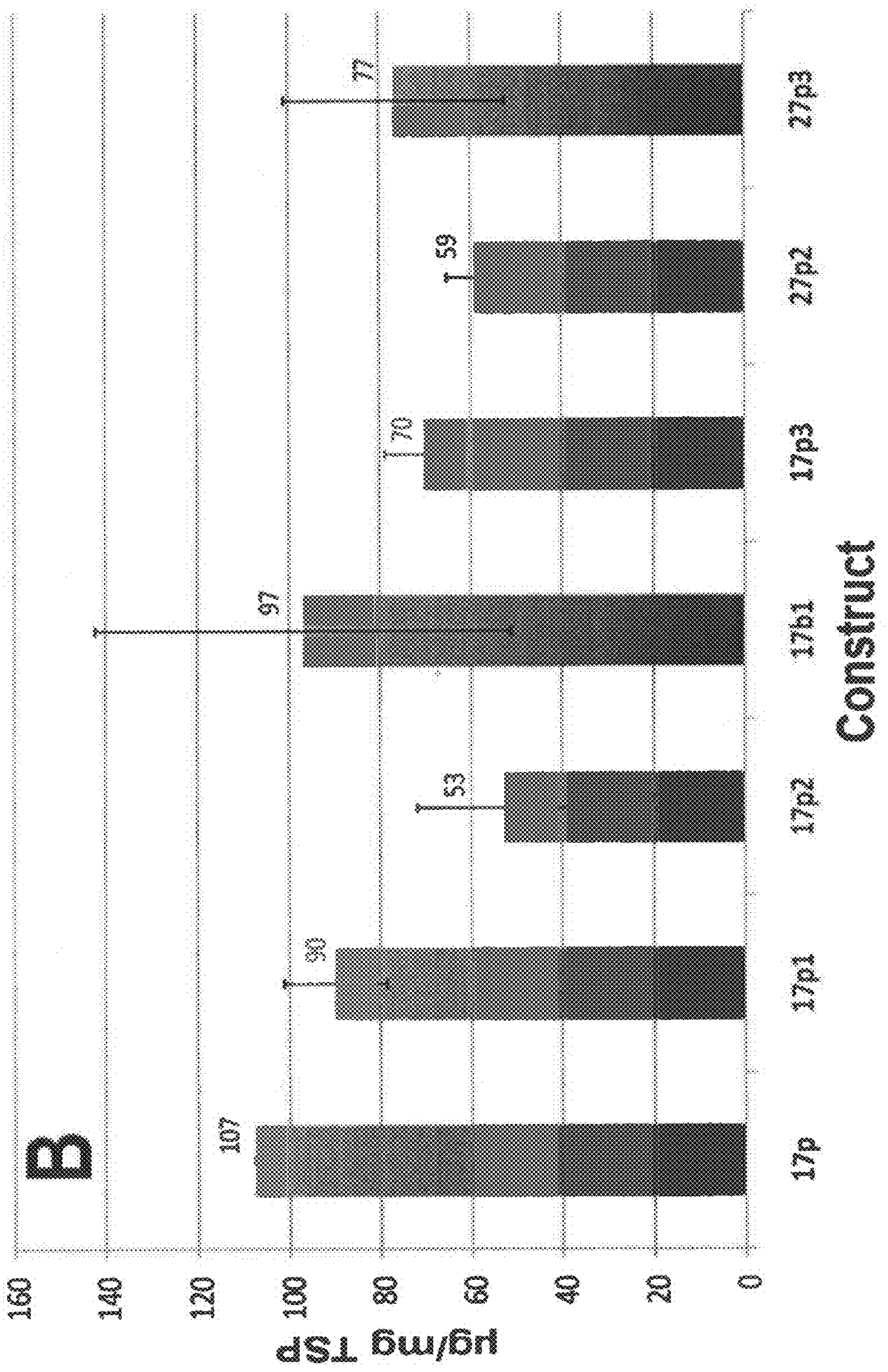

FIG. 3 depicts Rituximab expression levels using different geminiviral vectors. Each bar represents expression obtained in *N. benthamiana* leaf inoculated with the indicated construct, measured by ELISA for human IgG (gamma chain capture, kappa chain probe). Syringe-infiltrated leaf samples were harvested 3 days after delivery, extracted, and assayed for human IgG by ELISA. A: Data were calculated on the basis of leaf tissue mass. B, Data were calculated on the basis of total soluble protein (TSP). Data are means±S.D., n=3. Each replicate was an independent leaf sample. 17p: pBYR17p-MRtx; 17p1: pBYR17p1-MRtx; 17p2: pBYR17p2-MRtx; 17p3: pBYR17p3-MRtx; 17b1: pBYR17b1-MRtx; 27p2: pBYR27p2-MRtx; 27p3: pBYR27p3-MRtx.

Figure 4:
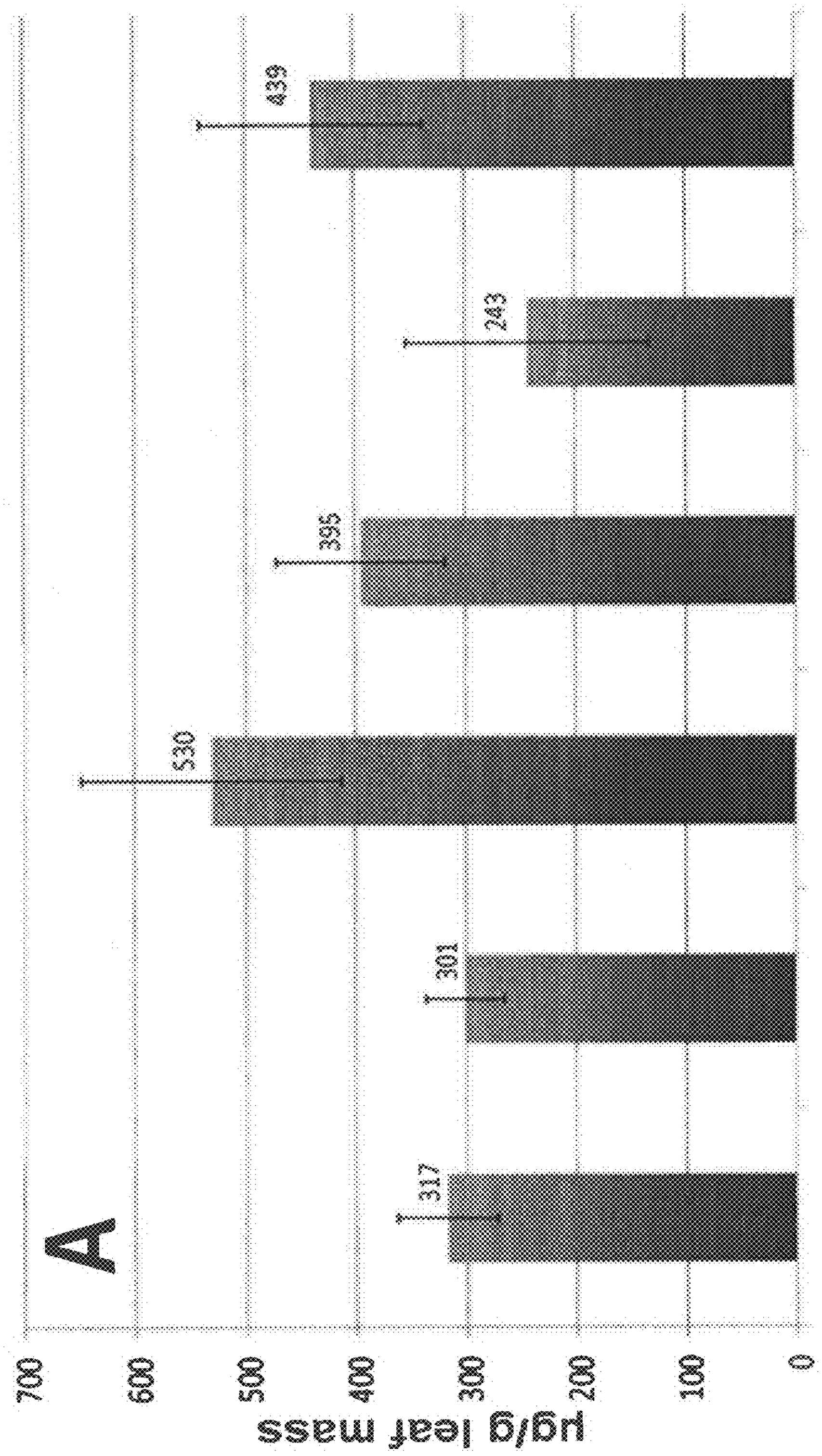
Figure 4:
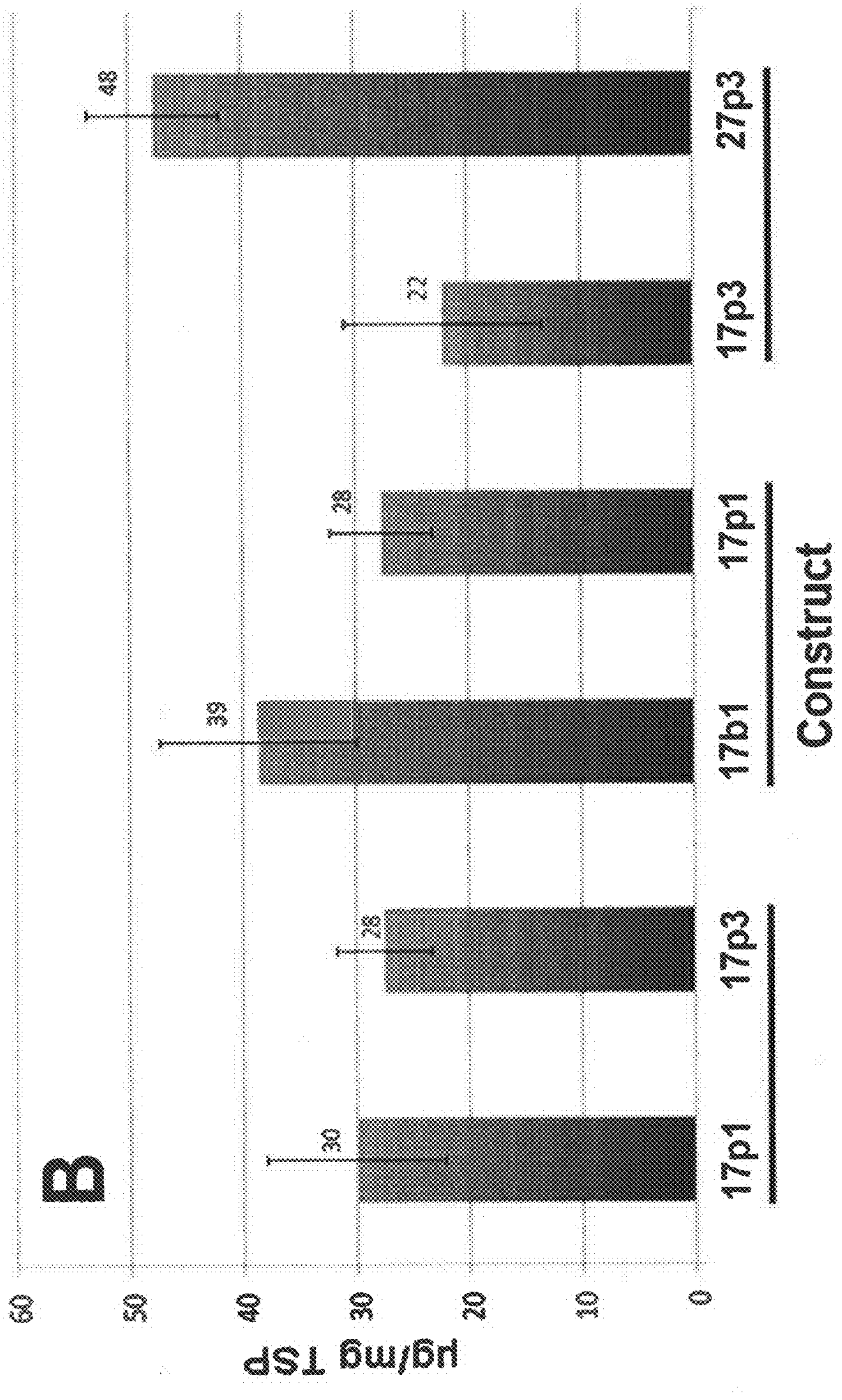

FIG. 4 depicts Rituximab expression levels by direct comparison of selected geminiviral vectors. Each bar represents expression obtained in *N. benthamiana* leaf inoculated with the indicated construct, measured by ELISA for human IgG (gamma chain capture, kappa chain probe). Four of the most promising constructs from the experiment of FIG. 3 were infiltrated pair-wise into opposite sides of the same leaf. Underlines indicate pairs of constructs in the same leaf. Syringe-infiltrated leaf samples were harvested 3 days after delivery, extracted, and assayed for human IgG by ELISA. A, Data are calculated on the basis of leaf tissue mass. B, Data are calculated on the basis of total soluble protein (TSP). Data are means±S.D., n=3. Each replicate was an independent leaf sample. 17p1: pBYR17p1-MRtx; 17p3: pBYR17p3-MRtx; 17b1: pBYR17b1-MRtx; 27p3: pBYR27p3-MRtx.

Figure 5:
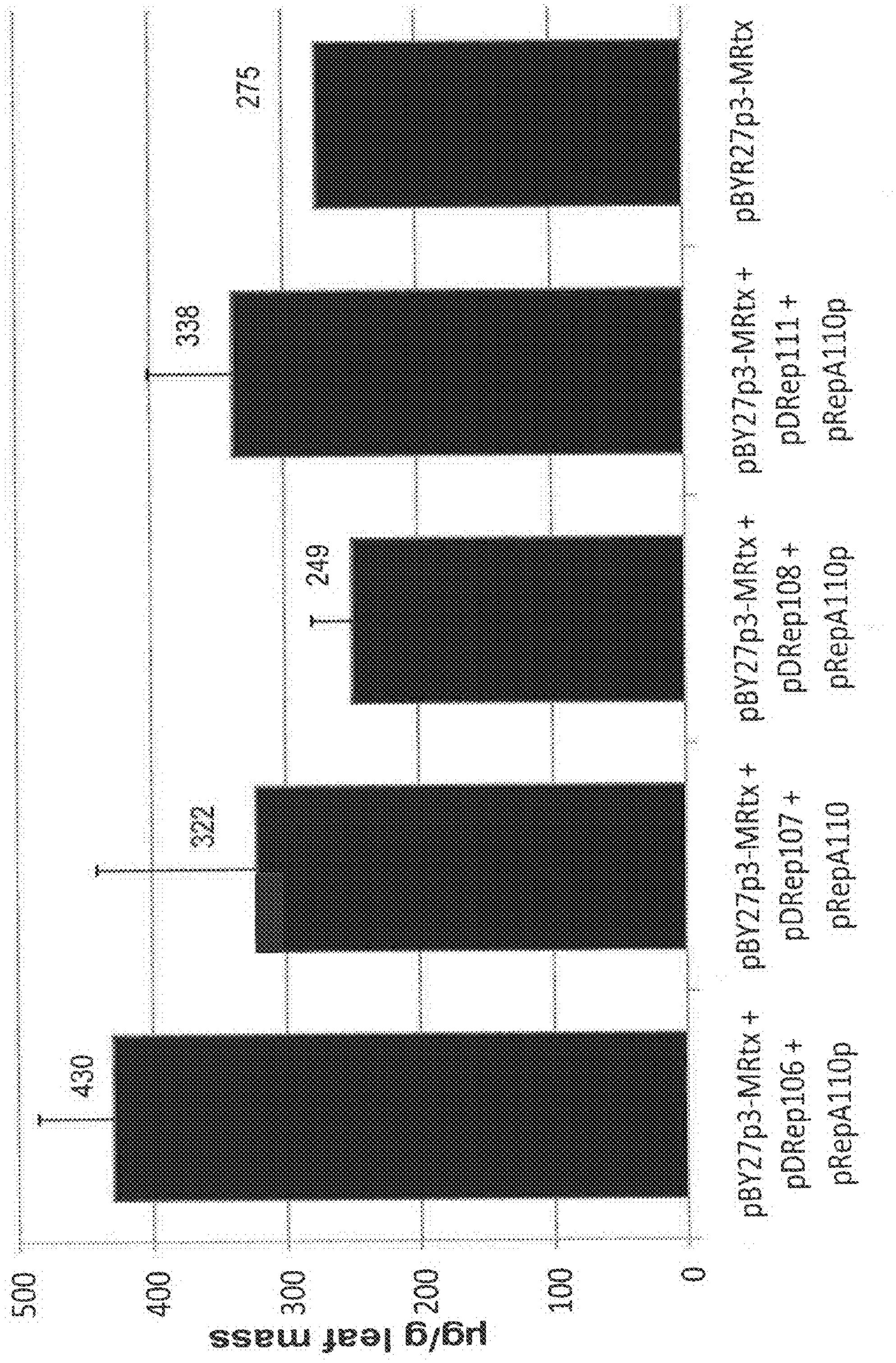

FIG. 5 depicts Rituximab expression levels using pBY27p3-MRtx (C1/C2 gene deleted) co-delivered with various combinations of vectors for expression of Rep and RepA. Each bar represents expression obtained in *N. benthamiana* leaf inoculated with the indicated set of constructs, measured by ELISA for human IgG (gamma chain capture, kappa chain probe). Data are calculated on the basis of leaf tissue mass, and data are means±S.D., n=2 (except pBYR27p3-MRtx, n=1). Each replicate was an independent leaf sample. Rep expression in the combination treatments was achieved using 4 different constructs (pDRep106, pDRep107, pDRep108, pDRep111) each having a different promoter. RepA expression in the combination treatments was achieved using pRepA110p.

Figure 6:
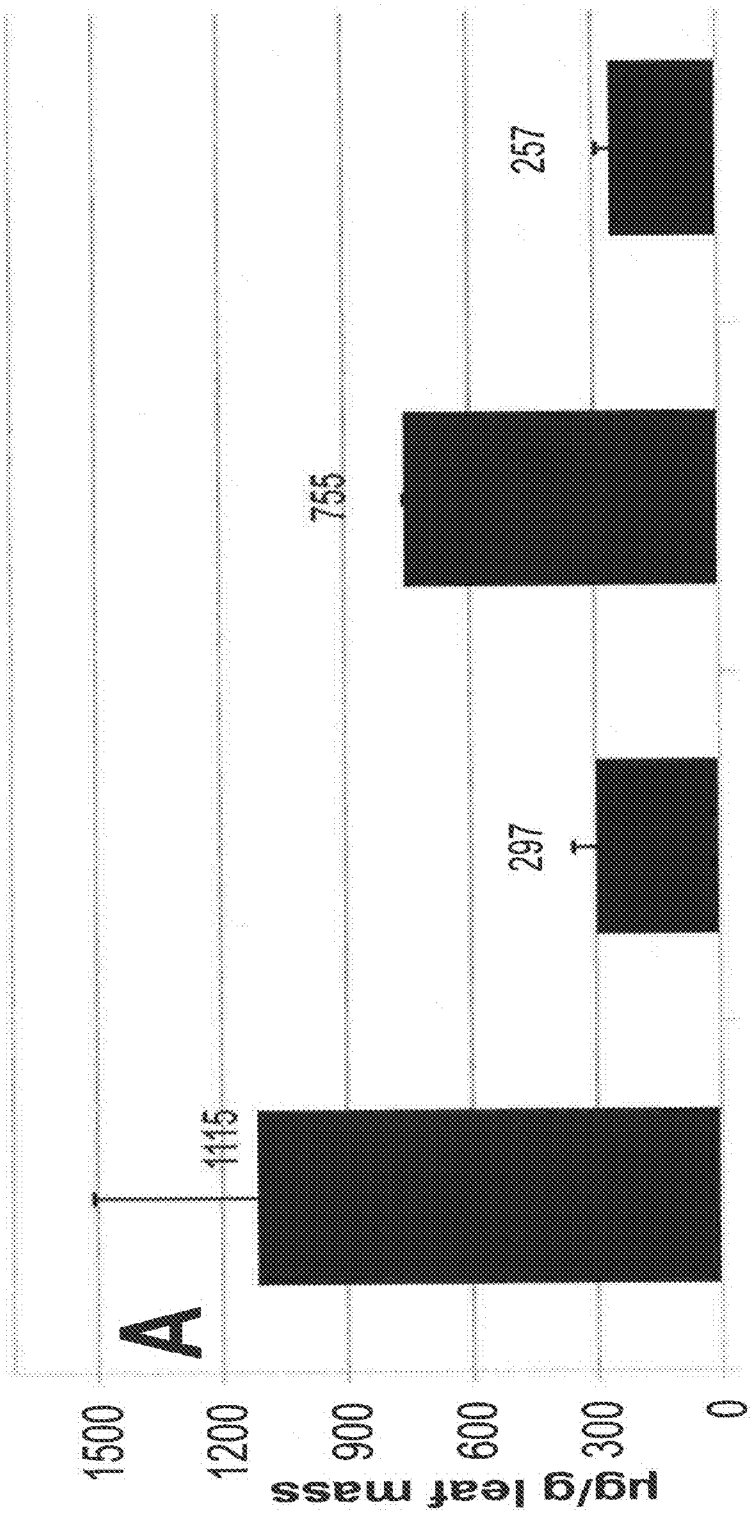
Figure 6:
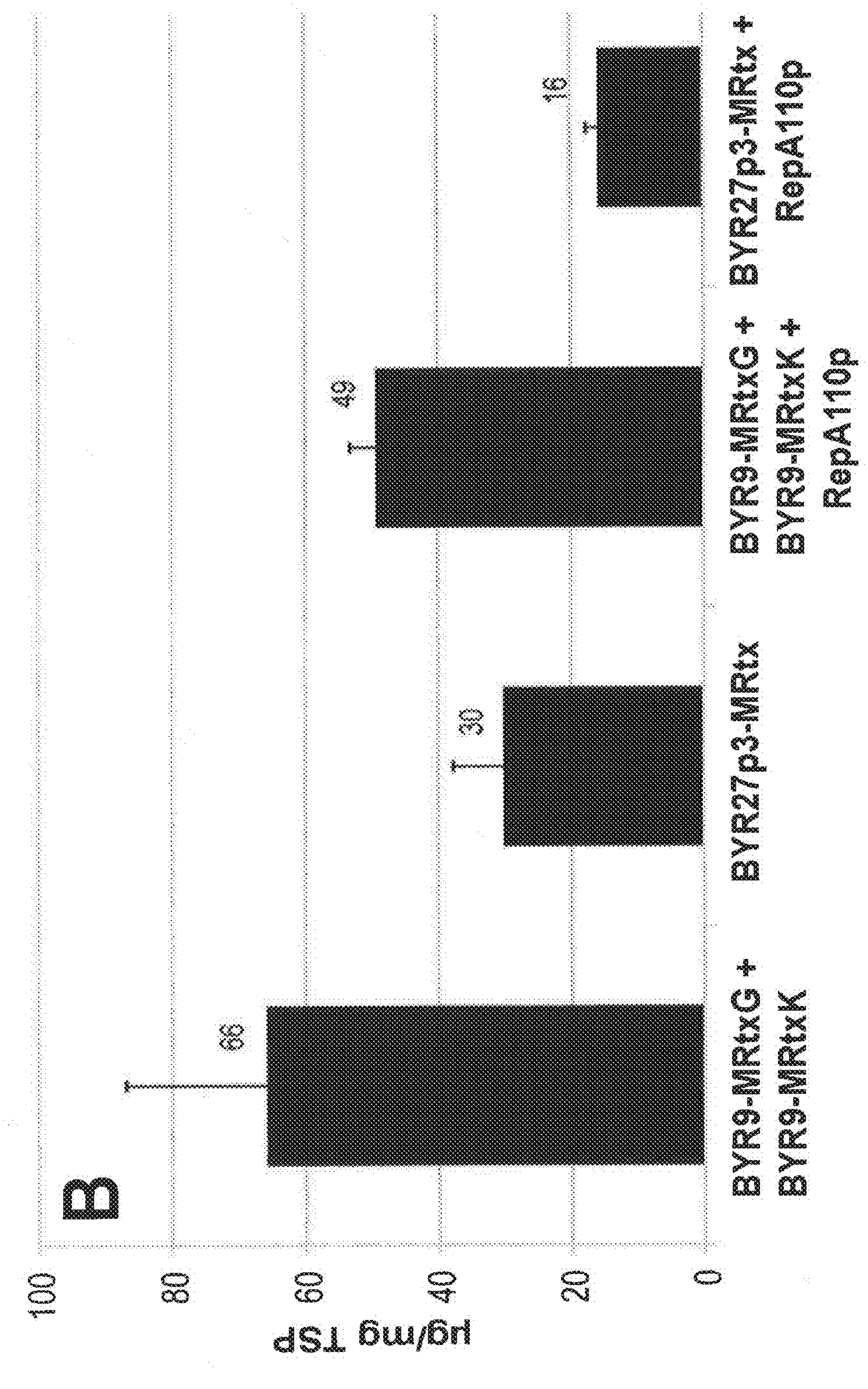

FIG. 6 depicts Rituximab expression levels by comparison of selected geminiviral vector combinations. Each bar represents expression obtained in *N. benthamiana* leaf inoculated with the indicated construct(s), measured by ELISA for human IgG (gamma chain capture, kappa chain probe). A: Data were calculated on the basis of leaf tissue mass. B: Data were calculated on the basis of total soluble protein (TSP). Data are means±S.D., n=6 for pBYR9-MRtxG+pBYR9-MRtxK and pBYR27p3-MRtx, or n=2 for pBYR9-MRtxG+pBYR9-MRtxK+pRepA110p and pBYR27p3-MRtx+pRepA110p. Each replicate was an independent leaf sample.

DETAILED DESCRIPTION OF THE INVENTION

The present invention provides an optimized geminiviral vector system for Rituximab expression in *N. benthamiana*.

Among the vectors constructed and tested, pBYR27p3-MRtx is an optimal construct that can be used in a multi-replicon single vector system for making a much higher level of fully assembled Rituximab in *Nicotiana benthamiana* leaves in comparison to other constructs tested.

I. GEMINIVIRUSES

The geminiviruses are a large and diverse family of plant DNA viruses, with circular single-stranded (ss) DNA genomes that replicate through circular double stranded DNA intermediates. See Hanley-Bowdoin et al (1999); Lazarowitz (1992); Timmermans et al (1994).

In particular, the geminiviruses replicate via a rolling circle mechanism, analogous to that used by ssDNA plasmids of gram positive microorganisms. The only exogenous protein required for replication is the viral replication initiation (Rep) protein encoded by a geminiviral replicase gene. This multifunctional protein initiates replication at a conserved stem loop structure found in the viral origin of replication by inducing a nick within a conserved nonanucleotide motif (TAATATTAJ, C) found in the intergenic loop sequence. Transcription of the viral genome is bidirectional with transcription initially within the intergenic (IR) region. Rep also has functions involved in controlling the plant cell cycle, and possibly also in modulating the expression of host genes involved in DNA replication (reviewed by Palmer et al, 1997b). The Rep protein can act in trans, that is, it need not be expressed by the viral replicon itself, but can be supplied from another extrachromosomal viral replicon, or even from a nuclear transgene (Hanley-Bowdoin et al, 1990). The cis requirements for viral replication are the viral intergenic region/s (IR), which contain sequences essential for initiation of rolling circle replication (the long intergenic region (LIR) of Mastreviruses, or the intergenic region of other geminiviruses) and synthesis of the complementary strand (the short IR (SIR) of Mastreviruses).

As used herein, "replicon", also known as "replicon cassette" or "geminiviral replicon", is defined as a linear DNA segment that is flanked on either side by a long intergenic region (LIR), and having a short intergenic region (SIR) between the two flanking LIR elements, such that a replicon has the structure: "LIR-SIR-LIR". One may insert an expression cassette (comprising a promoter-coding sequence-terminator) between the first LIR and SIR, to make a replicon having the structure "LIR-(promoter-coding sequence-terminator)-SIR-LIR". A replicon need not contain the C1/C2 genes encoding Rep and RepA, because Rep and RepA proteins may be provided by a second non-replicating expression cassette. Alternatively, the C1/C2 coding sequence may be inserted into the replicon, between the SIR and second LIR, with inverted orientation relative to the expression cassette that lies between the first LIR and SIR, i.e. having the structure: "LIR-(promoter-coding sequence-terminator)-SIR-C2/C1-LIR". In some embodiments, two juxtaposed separate replicons share one LIR in the middle, having the structure "LIR-(promoter-coding sequence 1-terminator)-SIR-LIR-(promoter-coding sequence 2-terminator)-SIR-LIR".

Until recently, it has been difficult to efficiently express heterooligomeric proteins with plant viral vectors, because co-delivery of viral vectors built on the same virus backbone always results in early segregation and subsequent preferential amplification of one of the vectors in one cell—a common scenario of "competing replicons" (Giritch et al., 2006; Dietrich and Maiss, 2003; Diveki et al., 2002; Hull and Plaskitt, 1970). This problem has been recently overcome by utilizing two sets of vectors derived from non-competing TMV and PVX, respectively (Giritch et al., 2006). However, this system requires co-infection of three construct modules per protein subunit (Giritch et al., 2006), which may present challenges when heterooligomeric proteins with more than two hetero-subunits (such as secretory IgA and IgM) are the pharmaceutical targets.

In the present invention, a single vector system carrying multiple replicons in making Rituximab was explored, tested and optimized such that the construct is minimal in size because of the sharing of a flanking LIR between tandemly linked replicons, the replicons are non-competing in making the chains of Rituximab, and the yield of fully assembled Rituximab is high.

II. NUCLEIC ACIDS

Some embodiments of this invention are directed to plant expression vectors comprising one or more vectors comprising a first nucleic acid segment comprising a promoter and a region encoding a product of interest, wherein the region encoding a product of interest is flanked on either side by at least a portion of a long intergenic region (LIR) of a geminivirus genome, and; a second nucleic acid segment comprising a promoter and a nucleic acid encoding a Rep/RepA protein of a geminivirus genome. The vectors may also comprise various additional components, including but not limited to those described above.

The term "nucleic acid" is well known in the art. As used in this application, the term "polynucleotide" refers to a nucleic acid molecule that either is recombinant or has been isolated free of total genomic nucleic acid. Included within the term "polynucleotide" are oligonucleotides (nucleic acids 100 residues or less in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be RNA, DNA, analogs thereof, or a combination thereof.

All types of genes may be expressed by the vector systems of the present invention. In this respect, the term "gene," "polynucleotide," or "nucleic acid" is used to refer to a nucleic acid that encodes a protein, polypeptide, or peptide (including any sequences required for proper transcription, post-translational modification, or localization). As will be understood by those in the art, this term encompasses genomic sequences, expression cassettes, cDNA sequences, and smaller engineered nucleic acid segments that express, or may be adapted to express, proteins, polypeptides, domains, peptides, fusion proteins, and mutants. A nucleic acid encoding all or part of a polypeptide may contain a contiguous nucleic acid sequence encoding all or a portion of such a polypeptide of the following lengths: 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1095, 1100, 1500, 2000, 2500, 3000, 3500, 4000, 4500, 5000, 5500, 6000, 6500, 7000, 7500, 8000, 9000, 10000, or more nucleotides, nucleosides, or base pairs of a polypeptide of the invention. It also is contemplated that a particular polypeptide may be encoded by nucleic acids containing variations having slightly different nucleic acid sequences but, nonetheless, encode the same or substantially similar protein.

The nucleic acid segments used in the present invention, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant nucleic acid protocol. In some cases, a nucleic acid sequence may encode a polypeptide sequence with additional heterologous coding sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a polypeptide that is not the same as the modified polypeptide.

It is contemplated that the nucleic acid constructs of the present invention may encode full-length polypeptide from any source or encode a truncated version of the polypeptide such that the transcript of the coding region represents the truncated version. The truncated transcript may then be translated into a truncated protein. Alternatively, a nucleic acid sequence may encode a full-length polypeptide sequence with additional heterologous coding sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a polypeptide that is not the same as the modified polypeptide.

In a non-limiting example, one or more nucleic acid constructs may be prepared that include a contiguous stretch of nucleotides identical to or complementary to a particular gene, such as the product of interest. A nucleic acid construct may be at least 20, 30, 40, 50, 60, 70, 80, 90, 100, 110, 120, 130, 140, 150, 160, 170, 180, 190, 200, 250, 300, 400, 500, 600, 700, 800, 900, 1,000, 2,000, 3,000, 4,000, 5,000, 6,000, 7,000, 8,000, 9,000, 10,000, 15,000, 20,000, 30,000, 50,000, 100,000, 250,000, 500,000, 750,000, to at least 1,000,000 nucleotides in length, as well as constructs of greater size, up to and including chromosomal sizes (including all intermediate lengths and intermediate ranges), given the advent of nucleic acids constructs such as a yeast artificial chromosome are known to those of ordinary skill in the art. It will be readily understood that "intermediate lengths" and "intermediate ranges," as used herein, means any length or range including or between the quoted values (i.e., all integers including and between such values).

The DNA segments used in the present invention encompass biologically functional equivalent modified polypeptides and peptides. Such sequences may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by human may be introduced through the application of site-directed mutagenesis techniques, e.g., to introduce improvements to the antigenicity of the protein, to reduce toxicity effects of the protein in vivo to a subject given the protein, or to increase the efficacy of any treatment involving the protein.

It also will be understood that this invention is not limited to the particular nucleic acid and amino acid sequences of the polynucleotide encoding the product of interest. Recombinant vectors and isolated DNA segments may therefore variously include the coding regions of the product of interest themselves, coding regions bearing selected alterations or modifications in the basic coding region, or they may encode larger polypeptides that nevertheless include coding regions of the product of interest or may encode biologically functional equivalent proteins or peptides that have variant amino acids sequences. If desired, one also may prepare fusion proteins and peptides, e.g., where the coding regions of the product of interest are aligned within the same expression unit with other proteins or peptides having desired functions, such as for purification or immunodetection purposes {e.g., proteins that may be purified by affinity chromatography and enzyme label coding regions, respectively).

Encompassed by certain embodiments of the present invention are DNA segments encoding relatively small peptides, such as, for example, peptides of from about 15 to about 50 amino acids in length, and more preferably, of from about 15 to about 30 amino acids in length; and also larger polypeptides up to and including proteins corresponding to the full-length published sequences for the product of interest.

Encompassed by certain embodiments of the invention are DNA segments encoding functional nucleic acid molecules, for example hybridization probes; amplification primers; siRNA, RNAi or antisense molecules; ribozymes; or RNA aptamers. In particular embodiments these functional nucleic acid molecules are identical or complementary to all or part of a nucleic acid sequence encoding the amino acid sequence of a product of interest. In other embodiments these functional nucleic acid molecules are identical or complementary to non-coding regions transcript of a product of interest or to nucleic acid "control sequences" that are required for the efficient expression of RNA or protein of a product of interest.

These definitions generally refer to a single-stranded molecule, but in specific embodiments will also encompass an additional strand that is partially, substantially or fully complementary to the single-stranded molecule. Thus, a nucleic acid may encompass a double-stranded molecule that comprises complementary strands or "complements" of a particular sequence comprising a molecule. In particular aspects, a nucleic acid encodes a protein or polypeptide, or a portion thereof.

A. Nucleic Acid Vectors

In particular embodiments, the invention concerns isolated DNA segments and recombinant vectors incorporating DNA sequences that encode a product of interest. The term "recombinant" may be used in conjunction with a polypeptide or the name of a specific polypeptide, and this generally refers to a polypeptide produced from a nucleic acid molecule that has been manipulated in vitro or that is the replicated product of such a molecule.

The term "vector" is used to refer to a carrier nucleic acid molecule into which a heterologous nucleic acid sequence can be inserted for introduction into a cell where it can be replicated and expressed. A nucleic acid sequence can be "heterologous," which means that it is in a context foreign to the cell in which the vector is being introduced or to the nucleic acid in which is incorporated, which includes a sequence homologous to a sequence in the cell or nucleic acid but in a position within the host cell or nucleic acid where it is ordinarily not found. Vectors include DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques (for example Sambrook et al, 2001; Ausubel et al, 1996, both incorporated herein by reference). Useful vectors encoding such fusion proteins include pIN vectors (Inouye et al, 1985), vectors encoding a stretch of histidines, and pGEX vectors, for use in generating glutathione S-transferase (GST) soluble fusion proteins for later purification and separation or cleavage.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

1. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. No. 4,683,202, U.S. Pat. No. 5,928,906, each incorporated herein by reference). Furthermore, it is contemplated that control sequences which direct transcription and/or expression of sequences within non-nuclear organelles such as mitochondria, chloroplasts, and the like, can be employed as well.

Naturally, it may be important to employ a promoter and/or enhancer that effectively directs the expression of the DNA segment in the cell type, organelle, and organism chosen for expression. Those of skill in the art of molecular biology know the general use of promoters, enhancers, and cell type combinations for protein expression, for example, see Sambrook et al (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous. The enhancer of the promoter may be a single enhancer or dual enhancer, which has duplicated enhancer region. Exemplary promoters and enhancers may derive from cauliflower mosaic virus, nopaline synthase, cassava vein mosaic virus, figwort mosaic virus, mannopine synthase, or octopine synthase, actin 1, ubiquitin, and plastocyanin genes.

The identity of tissue-specific promoters or elements, as well as assays to characterize their activity, is well known to those of skill in the art. Examples of such regions include control sequences associated with the human LIMK2 gene (Nomoto et al. 1999), the somatostatin receptor 2 gene (Kraus et al, 1998), murine epididymal retinoic acid-binding gene (Lareyre et al, 1999), human CD4 (Zhao-Emonet et al, 1998), mouse alpha2 (XI) collagen (Tsumaki, et al, 1998), DIA dopamine receptor gene (Lee, et al, 1997), insulin-like growth factor II (Wu et al, 1997), human platelet endothelial cell adhesion molecule-1 (Almendro et al, 1996), and the SM22α promoter.

2. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5'-methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

3. Multiple Cloning Sites

Vectors can include a multiple cloning site (MCS), which is a nucleic acid region that contains multiple restriction enzyme sites, any of which can be used in conjunction with standard recombinant technology to digest the vector. (See Carbonelli et al, 1999, Levenson et al, 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression. (See Chandler et al, 1997, incorporated herein by reference.)

5. Termination Signals

The vectors or constructs of the present invention will generally comprise at least one termination signal. A "termination signal" or "terminator" is comprised of the DNA sequences involved in specific termination of RNA transcription by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that the terminator comprises a signal for the cleavage of the RNA, and it is more preferred that the terminator signal promotes polyadenylation of the message. The terminator and/or polyadenylation site elements can serve to enhance message levels and/or to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

6. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the soybean vegetative storage protein (vspB) polyadenylation signal and/or pea RuBP carboxylase small subunit (rbcS) polyadenylation signal, convenient and/or known to function well in various plant target cells. Polyadenylation may increase the stability of the transcript or may facilitate cytoplasmic transport.

7. Origins of Replication

In order to propagate a vector in a host cell, it may contain one or more origin of replication sites (often termed "ori"), which is a specific nucleic acid sequence at which replication is initiated. Alternatively an autonomously replicating sequence (ARS) can be employed if the host cell is yeast.

8. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose selection is based on colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

B. Host Cells

Vectors of the invention may be used in a host cell to produce a product of interest. The particular, the vectors of the current invention may be a plant cell. As used herein, the terms "cell," "cell line," and "cell culture" may be used interchangeably. All of these terms also include their progeny, which includes any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid, such as a modified protein-encoding or functional nucleic acid encoding sequence, is transferred or introduced into the host cell. A transformed cell includes the primary subject cell and its progeny.

Host cells may be derived from prokaryotes or eukaryotes, including plant cells, yeast cells, insect cells, and mammalian cells, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM1 09, and K.C8, as well as a number of commercially available bacterial hosts such as SURE® Competent Cells and SOLOPACK™ Gold Cells (STRATAGENE®, La Jolla, Calif.). Alternatively, bacterial cells such as *E. coli* LE392 could be used as host cells for phage viruses. Appropriate yeast cells include *Saccharomyces cerevisiae, Saccharomyces pombe*, and *Pichia pastoris*.

Examples of eukaryotic host cells for replication and/or expression of a vector include HeLa, NIH3T3, Jurkat, 293, Cos, CHO, Saos, Sf9, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

C. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

In addition to the disclosed expression systems of the invention, other examples of expression systems include STRATAGENE®'S COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

1. Viral Vectors

There are a number of ways in which expression vectors may be introduced into cells. In certain embodiments of the invention, the expression vector comprises a virus or engineered vector derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubinstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubinstein, 1988; Temin, 1986).

The retroviruses are a group of single-stranded RNA viruses characterized by an ability to convert their RNA to double-stranded DNA in infected cells; they can also be used as vectors. Other viral vectors may be employed as expression constructs in the present invention. Vectors derived from viruses such as vaccinia virus (Ridgeway, 1988; Baichwal and Sugden, 1986; Coupar et al, 1988), adeno-associated virus (AAV) (Ridgeway, 1988; Baichwal and Sugden, 1986). Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

In addition to the disclosed expression systems of the invention, other examples of expression systems include STRATAGENE®'S COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-R.EX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

There are a number of ways in which expression vectors may be introduced into cells. In certain embodiments of the invention, the expression vector comprises a virus or engineered vector derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubinstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubinstein, 1988; Temin, 1986).

The retroviruses are a group of single-stranded RNA viruses characterized by an ability to convert their RNA to double-stranded DNA in infected cells; they can also be used as vectors. Other viral vectors may be employed as expression constructs in the present invention. Vectors derived from viruses such as vaccinia virus (Ridgeway, 1988; Baichwal and Sugden, 1986; Coupar et ah, 1988), adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et ah, 1988; Horwich et ah, 1990).

D. Methods of Gene Transfer

Suitable methods for nucleic acid delivery to effect expression of compositions of the present invention are believed to include virtually any method by which a nucleic acid (e.g., DNA, including viral and nonviral vectors) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al, 1990); by using DEAE-dextran followed by polyethylene glycol (Gopal, 1985); by direct sonic loading (Fechheimer et al, 1987); by liposome mediated transfection (Nicolau and Sene, 1982; Fraley et al, 1979; Nicolau et al, 1987; Wong et al, 1980; Kaneda et al, 1989; Kato et al, 1991); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al, 1990; U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); by PEG-mediated transformation of protoplasts (Omirulleh et αl, 1993; U.S. Pat. Nos. 4,684,611 and 4,952,500, each incorporated herein by reference); or by desiccation/inhibition-mediated DNA uptake (Potrykus et αl., 1985). Through the application of techniques such as these, organelle(s), cell(s), tissue(s) or organism(s) may be stably or transiently transformed.

E. Preparation of Nucleic Acids

One aspect of the present invention concerns isolated nucleic acid segments and their use in producing a product of interest in a plant cell. In certain embodiments, the present invention concerns nucleic acids encoding the proteins, polypeptides, peptides of the invention. A nucleic acid may be made by any technique known to one of ordinary skill in the art, such as for example, chemical synthesis, enzymatic production or biological production. Non-limiting examples of a synthetic nucleic acid (e.g., a synthetic oligonucleotide), include a nucleic acid made by in vitro chemical synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986 and U.S. Pat. No. 5,705,629, each incorporated herein by reference. In the methods of the present invention, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. No. 4,683,202 and U.S. Pat. No. 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced {i.e., replicated) in a living cell, such as a recombinant DNA vector replicated in bacteria (see for example, Sambrook et al. 2001, incorporated herein by reference).

F. Purification of Nucleic Acids

In certain aspects, the present invention concerns a nucleic acid that is an isolated nucleic acid. As used herein, the term "isolated nucleic acid" refers to a nucleic acid molecule {e.g., an RNA or DNA molecule) that has been isolated free of, or is otherwise free of, the bulk of the total genomic and transcribed nucleic acids of one or more cells. In certain embodiments, "isolated nucleic acid" refers to a nucleic acid that has been isolated free of, or is otherwise free of, bulk of cellular components or in vitro reaction components such as for example, macromolecules such as lipids or proteins, small biological molecules, and the like.

A nucleic acid may be purified on polyacrylamide gels, cesium chloride centrifugation gradients, chromatography columns or by any other means known to one of ordinary skill in the art (see for example, Sambrook et al, 2001, incorporated herein by reference). In some aspects, a nucleic acid is a pharmacologically acceptable nucleic acid. Pharmacologically acceptable compositions are known to those of skill in the art, and are described herein.

G. Nucleic Acid Detection

1. Hybridization

The use of a probe or primer of between 7, 8, 9, 10, 11, 12, 13, 14, 15, 16, 17, 18, 19, 20, 21, 22, 23, 24, 25, 50, 60, 70, 80, 90, or 100 nucleotides, preferably between 17 and 100 nucleotides in length, or in some aspects of the invention up to 1-2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

Accordingly, the nucleotide sequences of the invention may be used for their ability to selectively form duplex molecules with complementary stretches of DNAs and/or RNAs or to provide primers for amplification of DNA or RNA from samples. Depending on the application envisioned, one would desire to employ varying conditions of hybridization to achieve varying degrees of selectivity of the probe or primers for the target sequence.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting a specific polymorphism. It is generally appreciated that conditions can be rendered more stringent by the addition of increasing amounts of formamide. For example, under highly stringent conditions, hybridization to filter-bound DNA may be carried out in 0.5 M $NaHPO_4$, 7% sodium dodecyl sulfate (SDS), 1 mM EDTA at 65° C., and washing in 0.1× SSCVO.1% SDS at 68° C. (Ausubel et al, 1989).

Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Under low stringent conditions, such as moderately stringent conditions the washing may be carried out for example in 0.2×SSC/0.1% SDS at 42° C. (Ausubel et al, 1989). Hybridization conditions can be readily manipulated depending on the desired results. In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM MgCl2, at temperatures ranging from approximately 40° C. to about 72° C.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples. In other aspects, a particular nuclease cleavage site may be present and detection of a particular nucleotide sequence can be determined by the presence or absence of nucleic acid cleavage.

In general, it is envisioned that the probes or primers described herein will be useful as reagents in solution hybridization, as in PCR, for detection of expression or genotype of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

2. Amplification of Nucleic Acids

Nucleic acids used as a template for amplification may be isolated from cells, tissues or other samples according to standard methodologies (Sambrook et al, 2001). In certain embodiments, analysis is performed on whole cell or tissue homogenates or biological fluid samples with or without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to the SOD1 gene locus, variants and fragments thereof are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids that contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected, analyzed or quantified, in certain applications, the detection may be performed by visual means. In certain applications, the detection may involve indirect identification of the product via chemiluminescence, radioactive scintigraphy of incorporated radiolabel or fluorescent label or even via a system using electrical and/or thermal impulse signals (Affymax technology; Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al, 1988, each of which is incorporated herein by reference in their entirety. Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assay (OLA) (described in further detail below), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, Great Britain Application 2 202 328, and in PCT Application PCT/US89/01025, each of which is incorporated herein by reference in its entirety. Qbeta Replicase, described in PCT Application PCT/US87/00880, may also be used as an amplification method in the present invention.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al., 1989; PCT Application WO 88/10315, incorporated herein by reference in their entirety). European Application 329 822 disclose a nucleic acid amplification process involving cyclically synthesizing single-stranded RNA ("ssRNA"), ssDNA, and double-stranded DNA (dsDNA), which may be used in accordance with the present invention.

PCT Application WO 89/06700 (incorporated herein by reference in its entirety) discloses a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, 1990; Ohara et al, 1989).

3. Detection of Nucleic Acids

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et ah, 2001). Separated amplification products may be cut out and eluted from the gel for further manipulation. Using low melting point agarose gels, the separated band may be removed by heating the gel, followed by extraction of the nucleic acid.

Separation of nucleic acids may also be effected by spin columns and/or chromatographic techniques known in art. There are many kinds of chromatography which may be used in the practice of the present invention, including adsorption, partition, ion-exchange, hydroxyl apatite, molecular sieve, reverse-phase, column, paper, thin-layer, and gas chromatography as well as HPLC.

In certain embodiments, the amplification products are visualized, with or without separation. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art (see Sambrook et al., 2001). One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited for carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

III. PROTEINACEOUS COMPOSITIONS

It is contemplated that the product of interest may be a nucleic acid, protein, polypeptide, or peptide. The product of interest may include, but are not limited to, an antigen or an antibody. Examples of antigens include, but are not limited to, a hepatitis B core antigen (HBc) or a Norwalk Virus capsid protein (NVCP). Examples of antibodies include, but are not limited to, monoclonal antibodies.

In certain embodiments the product of interest is a protein, polypeptide or peptide. As used herein, a "protein," "proteinaceous molecule," "proteinaceous composition," "proteinaceous compound," "proteinaceous chain" or "proteinaceous material" generally refers, but is not limited to, a protein of greater than about 200 amino acids or the full length endogenous sequence translated from a gene; a polypeptide of greater than about 100 amino acids; and/or a peptide of from about 3 to about 100 amino acids. All the "proteinaceous" terms described above may be used interchangeably herein.

As used herein, a "protein" or "polypeptide" refers to a molecule comprising at least ten amino acid residues. In some embodiments, a wild-type version of a protein or polypeptide is employed, however, in many embodiments of the invention, a modified protein or polypeptide is employed to generate an immune response. The terms described above may be used interchangeably. A "modified protein" or "modified polypeptide" refers to a protein or polypeptide whose chemical structure, particularly its amino acid sequence, is altered with respect to the wild-type protein or polypeptide. It is specifically contemplated that a modified protein or polypeptide may be altered with respect to one activity or function yet retain a wild-type activity or function in other respects, such as immunogenicity.

In certain embodiments the size of a protein or polypeptide may comprise, but is not limited to, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1100, 1200, 1300, 1400, 1500, 1750, 2000, 2250, 2500 amino molecules or greater, and any range derivable therein, or derivative of a corresponding amino sequence described or referenced herein. It is contemplated that polypeptides may be mutated by truncation, rendering them shorter than their corresponding wild-type form, but also they might be altered by fusing or conjugating a heterologous protein sequence with a particular function (e.g., for targeting or localization, for enhanced immunogenicity, for purification purposes, etc.).

As used herein, an "amino molecule" refers to any amino acid, amino acid derivative, or amino acid mimic known in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties.

Accordingly, the term "proteinaceous composition" encompasses amino molecule sequences comprising at least one of the 20 common amino acids in naturally synthesized proteins, or at least one modified or unusual amino acid.

Proteinaceous compositions may be made by any technique known to those of skill in the art, including (i) the expression of proteins, polypeptides, or peptides through standard molecular biological techniques, (ii) the isolation of proteinaceous compounds from natural sources, or (iii) the chemical synthesis of proteinaceous materials. The nucleotide as well as the protein, polypeptide, and peptide sequences for various genes have been previously disclosed, and may be found in the recognized computerized databases. One such database is the National Center for Biotechnology Information's Genbank and GenPept databases (on the World Wide Web at ncbi.nlm.nih.gov/). The coding regions for these genes may be amplified and/or expressed using the techniques disclosed herein or as would be know to those of ordinary skill in the art.

A. Protein Purification

It may be desirable to purify or isolate the protein of interest. Protein purification techniques are well known to those of skill in the art. These techniques involve, at one level, the crude fractionation of the cellular milieu to polypeptide and non-polypeptide fractions. Having separated the polypeptide from other cellular components, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; affinity chromatography; polyacrylamide gel electrophoresis; and isoelectric focusing. A particularly efficient method of purifying peptides is fast protein liquid chromatography or even HPLC.

The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen and whether or not the expressed protein or peptide exhibits a detectable activity.

Various techniques suitable for use in protein purification will be well known to those of skill in the art. These include, for example, precipitation with ammonium sulfate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et ah, 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (e.g., altering pH, ionic strength, and temperature).

The matrix should be a substance that itself does not adsorb molecules to any significant extent and that has a broad range of chemical, physical and thermal stability. The ligand should be coupled in such a way as to not affect its binding properties. The ligand also should provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

B. Protein Detection

The protein of interest may be detected by any means known to those of skill in the art, including but not limited to those described below.

1. Immunodetection Methods

As discussed, in some embodiments, the present invention concerns immunodetection methods for binding, purifying, removing, quantifying and/or otherwise detecting biological components such as a protein of interest. The immunodetection methods of the present invention can be used to identify antigenic regions of a protein of interest that have therapeutic implications.

Immunodetection methods include enzyme linked immunosorbent assay (ELISA), radioimmunoassay (RIA), immunoradiometric assay, fluoroimmunoassay, chemiluminescent assay, bioluminescent assay, and Western blot, though several others are well known to those of ordinary skill. The steps of various useful immunodetection methods have been described in the scientific literature, such as, e.g., Doolittle et al., 1999; Gulbis et al, 1993; De Jager et al, 1993; and Nakamura et al, 1987, each incorporated herein by reference.

In general, the immunobinding methods include obtaining a sample suspected of containing a protein, polypeptide and/or peptide, and contacting the sample with a first antibody, monoclonal or polyclonal, in accordance with the present invention, as the case may be, under conditions effective to allow the formation of immunocomplexes.

These methods include methods for purifying a protein, polypeptide and/or peptide from organelle, cell, tissue or organism's samples. In these instances, the antibody removes the antigenic protein, polypeptide and/or peptide component from a sample. The antibody will preferably be linked to a solid support, such as in the form of a column matrix, and the sample suspected of containing the protein, polypeptide and/or peptide antigenic component will be applied to the immobilized antibody. The unwanted components will be washed from the column, leaving the antigen immunocomplexed to the immobilized antibody to be eluted.

The immunobinding methods also include methods for detecting and quantifying the amount of an antigen component in a sample and the detection and quantification of any immune complexes formed during the binding process. Here, one would obtain a sample suspected of containing an antigen or antigenic domain, and contact the sample with an antibody against the antigen or antigenic domain, and then detect and quantify the amount of immune complexes formed under the specific conditions.

In terms of antigen detection, the biological sample analyzed may be any sample that is suspected of containing an antigen or antigenic domain, such as, for example, a tissue section or specimen, a homogenized tissue extract, a cell, an organelle, separated and/or purified forms of any of the above antigen-containing compositions, or even any biological fluid that comes into contact with the cell or tissue, including blood and/or serum.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any antigens present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as radioactive, fluorescent, biological and enzymatic tags. U.S. Patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection designed by Charles Cantor uses two different antibodies. A first step biotinylated, monoclonal or polyclonal antibody is used to detect the target antigen(s), and a second step antibody is then used to detect the biotin attached to the antibody/antigen complex, hi this method the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

a. ELISAs

As detailed above, immunoassays, in their most simple and/or direct sense, are binding assays. Certain preferred immunoassays are the various types of enzyme linked immunosorbent assays (ELISAs) and/or radioimmunoassays (RIA) known in the art. Immunohistochemical detection using tissue sections is also particularly useful. However, it will be readily appreciated that detection is not limited to such techniques, and/or western blotting, dot blotting, FACS analyses, and/or the like may also be used.

In one exemplary ELISA, antibodies are immobilized onto a selected surface exhibiting protein affinity, such as a well in a polystyrene microtiter plate. Then, a test composition suspected of containing the antigen, such as a clinical sample, is added to the wells. After binding and/or washing to remove non-specifically bound immune complexes, the bound antigen may be detected. Detection is generally achieved by the addition of another antibody that is linked to a detectable label. This type of ELISA is a simple "sandwich ELISA." Detection may also be achieved by the addition of a second antibody, followed by the addition of a third antibody that has binding affinity for the second antibody, with the third antibody being linked to a detectable label.

In another exemplary ELISA, the samples suspected of containing the antigen are immobilized onto the well surface and/or then contacted with antibodies. After binding and/or washing to remove non-specifically bound immune complexes, the bound antibodies are detected. Where the initial antibodies are linked to a detectable label, the immune complexes may be detected directly. Again, the immune complexes may be detected using a second antibody that has binding affinity for the first antibody, with the second antibody being linked to a detectable label.

Another ELISA in which the antigens are immobilized, involves the use of antibody competition in the detection. In this ELISA, labeled antibodies against an antigen are added to the wells, allowed to bind, and/or detected by means of their label. The amount of an antigen in an unknown sample is then determined by mixing the sample with the labeled antibodies against the antigen during incubation with coated wells. The presence of an antigen in the sample acts to reduce the amount of antibody against the antigen available for binding to the well and thus reduces the ultimate signal. This is also appropriate for detecting antibodies against an antigen in an unknown sample, where the unlabeled antibodies bind to the antigen-coated wells and also reduces the amount of antigen available to bind the labeled antibodies.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, or a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)ΛTween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. An example of a washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. This may be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

b. Immunohistochemistry

The antibodies of the present invention may also be used in conjunction with both fresh-frozen and/or formalin-fixed, paraffin-embedded tissue blocks prepared for study by immunohistochemistry (IHC). For example, immunohistochemistry may be utilized to characterize the protein of interest or to evaluate the amount the protein of interest in a cell. The method of preparing tissue blocks from these particulate specimens has been successfully used in previous IHC studies of various prognostic factors, and/or is well known to those of skill in the art (Brown et al, 1990; Abbondanzo et al, 1990; Allied et al, 1990).

Immunohistochemistry or IHC refers to the process of localizing proteins in cells of a tissue section exploiting the principle of antibodies binding specifically to antigens in biological tissues. It takes its name from the roots "immuno," in reference to antibodies used in the procedure, and "histo," meaning tissue. Immunohistochemical staining is widely used in the diagnosis and treatment of cancer. Specific molecular markers are characteristic of particular cancer types.

Visualizing an antibody-antigen interaction can be accomplished in a number of ways. In the most common instance, an antibody is conjugated to an enzyme, such as peroxidase, that can catalyse a colour-producing reaction. Alternatively, the antibody can also be tagged to a fluorophore, such as FITC, rhodamine, Texas Red, Alexa Fluor, or DyLight Fluor. The latter method is of great use in confocal laser scanning microscopy, which is highly sensitive and can also be used to visualize interactions between multiple proteins.

Briefly, frozen-sections may be prepared by rehydrating 50 mg of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections.

There are two strategies used for the immmunohistochemical detection of antigens in tissue, the direct method and the indirect method. In both cases, the tissue is treated to rupture the membranes, usually by using a detergent, such as Triton X-IOO.

The direct method is a one-step staining method, and involves a labeled antibody (e.g. FITC conjugated antiserum) reacting directly with the antigen in tissue sections. This technique utilizes only one antibody and the procedure is therefore simple and rapid. However, it can suffer problems with sensitivity due to little signal amplification and is in less common use than indirect methods.

The indirect method involves an unlabeled primary antibody (first layer) which reacts with tissue antigen, and a labeled secondary antibody (second layer) which reacts with the primary antibody. This method is more sensitive due to signal amplification through several secondary antibody reactions with different antigenic sites on the primary antibody. The second layer antibody can be labeled with a fluorescent dye or an enzyme.

In a common procedure, a biotinylated secondary antibody is coupled with streptavidin-horseradish peroxidase. This is reacted with 3,3'-Diaminobenzidine (DAB) to produce a brown staining wherever primary and secondary antibodies are attached in a process known as DAB staining. The reaction can be enhanced using nickel, producing a deep purple/gray staining. The indirect method, aside from its greater sensitivity, also has the advantage that only a relatively small number of standard conjugated (labeled) secondary antibodies needs to be generated. For example, a labeled secondary antibody raised against rabbit IgG, which can be purchased "off the shelf," is useful with any primary antibody raised in a rabbit. With the direct method, it would be necessary to make custom labeled antibodies against every antigen of interest.

c. Protein Arrays

Protein array technology is discussed in detail in Pandey and Mann (2000) and MacBeath and Schreiber (2000), each of which is herein specifically incorporated by reference.

These arrays typically contain thousands of different proteins or antibodies spotted onto glass slides or immobilized in tiny wells and allow one to examine the biochemical activities and binding profiles of a large number of proteins at once. To examine protein interactions with such an array, a labeled protein is incubated with each of the target proteins immobilized on the slide, and then one determines which of the many proteins the labeled molecule binds. In certain embodiments such technology can be used to quantitate a number of proteins in a sample, such as a protein of interest.

The basic construction of protein chips has some similarities to DNA chips, such as the use of a glass or plastic surface dotted with an array of molecules. These molecules can be DNA or antibodies that are designed to capture proteins. Defined quantities of proteins are immobilized on each spot, while retaining some activity of the protein. With fluorescent markers or other methods of detection revealing the spots that have captured these proteins, protein microarrays are being used as powerful tools in high-throughput proteomics and drug discovery.

The earliest and best-known protein chip is the ProteinChip by Ciphergen Biosystems Inc. (Fremont, Calif.). The ProteinChip is based on the surface-enhanced laser desorption and ionization (SELDI) process. Known proteins are analyzed using functional assays that are on the chip. For example, chip surfaces can contain enzymes, receptor proteins, or antibodies that enable researchers to conduct protein-protein interaction studies, ligand binding studies, or immunoassays. With state-of-the-art ion optic and laser optic technologies, the ProteinChip system detects proteins ranging from small peptides of less than 1000 Da up to proteins of 300 kDa and calculates the mass based on time-of-flight (TOF). The ProteinChip biomarker system is the first protein biochip-based system that enables biomarker pattern recognition analysis to be done. This system allows researchers to address important clinical questions by investigating the proteome from a range of crude clinical samples (i.e., laser capture microdissected cells, biopsies, tissue, urine, and serum). The system also utilizes biomarker pattern software that automates pattern recognition-based statistical analysis methods to correlate protein expression patterns from clinical samples with disease phenotypes.

C. Protective Immunity

In some embodiments of the invention, the protein of interest can raise an immune response in a subject. Protective immunity refers to a body's ability to mount a specific immune response that protects the subject from developing a particular disease or condition that involves the agent against which there is an immune response. An immunogenically effective amount is capable of conferring protective immunity to the subject.

As used herein in the specification and in the claims section that follows, the term polypeptide refers to a stretch of amino acids covalently linked there amongst via peptide bonds. Different polypeptides have different functionalities according to the present invention. While according to one aspect a polypeptide is derived from an immunogen designed to induce an active immune response in a recipient, according to another aspect of the invention, a polypeptide is derived from an antibody which results following the elicitation of an active immune response, in, for example, an animal, and which can serve to induce a passive immune response in the recipient. In both cases, however, the polypeptide is encoded by a polynucleotide according to any possible codon usage.

As used herein the phrase "immune response" or its equivalent "immunological response" refers to the development of a humoral (antibody mediated), cellular (mediated by antigen-specific T cells or their secretion products) or both humoral and cellular response directed against a protein, peptide, or polypeptide of the invention in a recipient patient. Such a response can be an active response induced by administration of immunogen or a passive response induced by administration of antibody, antibody containing material, or primed T-cells. A cellular immune response is elicited by the presentation of polypeptide epitopes in association with Class I or Class II MHC molecules, to activate antigen-specific CD4 (+) T helper cells and/or CD8 (+) cytotoxic T cells. The response may also involve activation of monocytes, macrophages, NK cells, basophils, dendritic cells, astrocytes, microglia cells, eosinophils or other components of innate immunity. As used herein "active immunity" refers to any immunity conferred upon a subject by administration of an antigen.

As used herein "passive immunity" refers to any immunity conferred upon a subject without administration of an antigen to the subject. "Passive immunity" therefore includes, but is not limited to, administration of activated immune effectors including cellular mediators or protein mediators (e.g., monoclonal and/or polyclonal antibodies) of an immune response. A monoclonal or polyclonal antibody composition may be used in passive immunization for the prevention or treatment of infection by organisms that carry the antigen recognized by the antibody. An antibody composition may include antibodies that bind to a variety of antigens that may in turn be associated with various organisms. The antibody component can be a polyclonal antiserum. In certain aspects the antibody or antibodies are affinity purified from an animal or second subject that has been challenged with an antigen(s). Alternatively, an antibody mixture may be used, which is a mixture of monoclonal and/or polyclonal antibodies to antigens present in the same, related, or different microbes or organisms, such as gram-positive bacteria, gram-negative bacteria, including but not limited to *staphylococcus* bacteria.

Passive immunity may be imparted to a patient or subject by administering to the patient immunoglobulins (Ig) and/or other immune factors obtained from a donor or other non-patient source having a known immunoreactivity. In other aspects, an antigenic composition of the present invention can be administered to a subject who then acts as a source or donor for globulin, produced in response to challenge from the composition ("hyperimmune globulin"), that contains antibodies directed against *Staphylococcus* or other organism. A subject thus treated would donate plasma from which hyperimmune globulin would then be obtained, via conventional plasma-fractionation methodology, and administered to another subject in order to impart resistance against or to treat *staphylococcus* infection. Hyperimmune globulins according to the invention are particularly useful for immune-compromised individuals, for individuals undergoing invasive procedures or where time does not permit the individual to produce his own antibodies in response to vaccination. See U.S. Pat. Nos. 6,936,258, 6,770,278, 6,756,361, 5,548,066, 5,512,282, 4,338,298, and 4,748,018, each of which is incorporated herein by reference in its entirety, for exemplary methods and compositions related to passive immunity.

For purposes of this specification and the accompanying claims the terms "epitope" and "antigenic determinant" are used interchangeably to refer to a site on an antigen to which B and/or T cells respond or recognize. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols (1996). Antibodies that recognize the same epitope can be identified in a simple immunoassay showing the ability of one antibody to block the binding of another antibody to a target antigen. T-cells recognize continuous epitopes of about nine amino acids for CD8 cells or about 13-15 amino acids for CD4 cells. T cells that recognize the epitope can be identified by in vitro assays that measure antigen-dependent proliferation, as determined by $^3$H-thymidine incorporation by primed T cells in response to an epitope (Burke et al., 1994), by antigen-dependent killing (cytotoxic T lymphocyte assay, Tigges et al, 1996) or by cytokine secretion.

The presence of a cell-mediated immunological response can be determined by proliferation assays (CD4 (+) T cells) or CTL (cytotoxic T lymphocyte) assays. The relative contributions of humoral and cellular responses to the protective or therapeutic effect of an immunogen can be distinguished by separately isolating IgG and T-cells from an immunized syngeneic animal and measuring protective or therapeutic effect in a second subject.

As used herein and in the claims, the terms "antibody" or "immunoglobulin" are used interchangeably and refer to any of several classes of structurally related proteins that function as part of the immune response of an animal or recipient, which proteins include IgG, IgD, IgE, IgA, IgM and related proteins.

Under normal physiological conditions antibodies are found in plasma and other body fluids and in the membrane of certain cells and are produced by lymphocytes of the type denoted B cells or their functional equivalent. Antibodies of the IgG class are made up of four polypeptide chains linked together by disulfide bonds. The four chains of intact IgG molecules are two identical heavy chains referred to as H-chains and two identical light chains referred to as L-chains.

In order to produce polyclonal antibodies, a host, such as a rabbit or goat, is immunized with the antigen or antigen fragment, generally with an adjuvant and, if necessary, coupled to a carrier. Antibodies to the antigen are subsequently collected from the sera of the host. The polyclonal antibody can be affinity purified against the antigen rendering it monospecific. In order to produce monoclonal antibodies, hyperimmunization of an appropriate donor, generally a mouse, with the antigen is undertaken. Isolation of splenic antibody producing cells is then carried out. These cells are fused to a cell characterized by immortality, such as a myeloma cell, to provide a fused cell hybrid (hybridoma) which can be maintained in culture and which secretes the required monoclonal antibody. The cells are then be cultured, in bulk, and the monoclonal antibodies harvested from the culture media for use. By definition, monoclonal antibodies are specific to a single epitope. Monoclonal antibodies often have lower affinity constants than polyclonal antibodies raised against similar antigens for this reason.

Monoclonal antibodies may also be produced ex-vivo by use of primary cultures of splenic cells or cell lines derived from spleen. In order to produce recombinant antibody (see generally Huston et al, 1991; Johnson et al, 1991; Mernaugh et al, 1995), messenger RNAs from antibody producing B-lymphocytes of animals, or hybridoma are reverse-transcribed to obtain complementary DNAs (cDNAs). Antibody cDNA, which can be full length or partial length, is amplified and cloned into a phage or a plasmid. The cDNA can be a partial length of heavy and light chain cDNA, separated or connected by a linker. The antibody, or antibody fragment, is expressed using a suitable expression system to obtain recombinant antibody. Antibody cDNA can also be obtained by screening pertinent expression libraries.

The antibody can be bound to a solid support substrate or conjugated with a detectable moiety or be both bound and conjugated as is well known in the art. For a general discussion of conjugation of fluorescent or enzymatic moieties see Johnstone et al. (1982). The binding of antibodies to a solid support substrate is also well known in the art (Harlow et al, 1988; Borrebaeck, 1992).

As used herein and in the claims, the phrase "an immunological portion of an antibody" include a Fab fragment of an antibody, a Fv fragment of an antibody, a heavy chain of an antibody, a light chain of an antibody, an unassociated mixture of a heavy chain and a light chain of an antibody, a heterodimer consisting of a heavy chain and a light chain of an antibody, a catalytic domain of a heavy chain of an antibody, a catalytic domain of a light chain of an antibody, a variable fragment of a light chain of an antibody, a variable fragment of a heavy chain of an antibody, and a single chain variant of an antibody, which is also known as scFv. In addition, the term includes chimeric immunoglobulins which are the expression products of fused genes derived from different species, one of the species can be a human, in which case a chimeric immunoglobulin is said to be humanized. Typically, an immunological portion of an antibody competes with the intact antibody from which it was derived for specific binding to an antigen.

Optionally, an antibody or preferably an immunological portion of an antibody, can be chemically conjugated to, or expressed as, a fusion protein with other proteins. For purposes of this specification and the accompanying claims, all such fused proteins are included in the definition of antibodies or an immunological portion of an antibody.

As used herein the terms "immunogenic agent" or "immunogen" or "antigen" are used interchangeably to describe a molecule capable of inducing an immunological response against itself on administration to a recipient, either alone, in conjunction with an adjuvant, or presented on a display vehicle.

IV. EXAMPLES

The following examples are included to demonstrate certain non-limiting aspects of the invention.

Example 1: Construction of Expression Vectors

The expression vectors were based upon the geminiviral replicons previously described (Huang et al., *Biotechnol. Bioeng.* 106: 9-17, 2010). New features were introduced, including unique restriction sites flanking the heavy and light chain coding regions, and the use of the tobacco extensin (Ext) gene terminator region (Genbank accession D13951), which was found to perform better than many commonly used terminators (S-H Rosenthal & H. S. Mason, manuscript in preparation). The Ext terminator was amplified from *Nicotiana tabacum* genomic DNA using primers Ext-1 (5'-GTGAGCTCGAAGTGACATCACAAAGTTGAAG; SEQ ID NO. 1) and Ext-2 (5'-CAGAATTCGTCATAACTGTAGAAATGATTCC; SEQ ID NO. 2), digested with SacI-EcoRI, and inserted into the same sites of pBYGFP.R (Huang et al., *Biotechnol. Bioeng.* 103: 706-714, 2009). The GFP coding sequence in the resulting plasmid was replaced with a section of the pUC19 polylinker to introduce the restriction enzyme sites XbaI-BamHI-SmaI-KpnI-SacI between the TEV 5' UTR and the Ext terminator, to yield pBYR1.

In the dual replicon vector pBY-HL(6D8).R (Huang et al., 2010), the NPTII expression cassette near the left border was replaced by cleaving the plasmid with PvuI and AscI, and inserting annealed complementary nucleotides that comprise the sequence CGATCGACACTAGTAAGCTGGCGCGC (pBY-HL(6D8).R insertion sequence; SEQ ID NO. 3) and contain the restriction sites PvuI-SpeI-AscI. The light chain coding sequence was replaced by the sequence TGTACAACAGGTACC (pBY-HL(6D8).R light chain replacement sequence; SEQ ID NO. 4) containing the restriction sites BsrGI (unique site) and KpnI, in order to facilitate insertion of other coding sequences. The expression cassette from pBYR1 comprising the CaMV 35S (dual enhancer) promoter, TEV 5'UTR, and Ext terminator, was substituted for the 6D8 heavy chain cassette in pBY-HL(6D8).R, to yield pBYR27b (FIG. 1A). In addition to LIR-C1/C2/SIR, pBYR27b comprises two expression cassettes. The first expression cassette, with a flanking LIR and a flanking SIR, comprises the CaMV 35S promoter (with dual enhancer, 35S×2e), TEV 5'UTR, and Ext terminator. Whereas the second cassette, with a flanking LIR and a flanking SIR, comprises the CaMV 35S (dual enhancer) promoter (35S×2e), TMV 5'UTR, and rbcS terminator.

An expression cassette for the RNAi silencing inhibitor p19 was constructed, by inserting the p19 coding sequence (gift of H. Scholthof) between a nopaline synthase (NOS) promoter (pNOS) and a terminator (Nos 3'), flanked by PvuI and AscI sites. The cassette was then inserted into the PvuI-AscI sites of pBYR27b, yielding pBYR27p (FIG. 1B).

A single replicon vector containing the same two expression cassettes in pBYR27p was constructed by deletion of the segment containing the geminiviral long and short intergenic regions (LIR, SIR) located between the EcoRI site at the 3' end of the Ext terminator and the PstI site at the 5' end to the second 35S promoter, such that cassette 1 of pBYR27b has only the flanking LIR, and cassette 2 of pBYR27b has only the flanking SIR. After ligating the Klenow-filled EcoRI site with the PstI site made blunt using T4 DNA polymerase, the two expression cassettes was linked operatively in tandem between one flanking LIR and one flanking SIR element, such that a single geminiviral replicon was generated, and with the vector named as pBYR17p (FIG. 1C).

The Rituximab plant-optimized heavy and light chain coding sequences were first fused to the barley alpha amylase N-terminal signal peptide coding sequence from Mapp Biopharmaceutical (San Diego, Calif.). The heavy chain gene was end-tailored to create 5' XbaI and 3' SacI sites, using high-fidelity PCR with the primers BAA-Xba-F (5'-CCTCTAGAACAATGGCTAACAAACATCTTTCTTTG; SEQ ID NO. 5) and RituxG-Sac-R (5'-CCGAGCTCTTACTTACCAGGTGAAAGAGAC; SEQ ID NO. 6). The resulting product was digested with XbaI-SacI and ligated with pBYR17p digested likewise, to yield pBYR17p-MRtxG (FIG. 1D. The Rituximab light chain coding sequence was then end-tailored by PCR to create 5' BsrGI and 3' KpnI sites using the primers BAA-Bsr-F (5'-CCTGTACAACAATGGCTAACAAACATCTTTCTTTG; SEQ ID NO. 7) and RituxK-Kpn-R (5'-GCGGTACCTTAGCACTCTCCCCTATTAAAAG; SEQ ID NO. 8). The resulting product was digested with BsrGI-KpnI and ligated with pBYR17p-MRtxG digested likewise, yielding pBYR17p-MRtx (FIG. 1E).

The 35S promoters used in pBYR17p contain duplicated enhancer regions. In order to minimize the length of repeated DNA that could effect recombination to delete sequences, pBYR17p-MRtx was modified to create pBYR17p1-MRtx (FIG. 1F), in which the two dual enhancer 35S promoters were replaced with two single enhancer 35S promoters. To achieve that, four fragments were ligated together to make pBYR17p1-MRtx: 1) vector pBYR17p-MRtx cut with AscI-BsrGI, 2) the AscI-XbaI fragment from pBY-HL(6D8).R containing LIR, single-enhancer 35S promoter, and TEV 5' UTR, 3) the XbaI-SacI fragment from pBYR17p-MRtx containing the H chain cds, and 4) the SacI-BsrGI fragment from subclone pUC-NpE35SΩ!Mfe containing Ext terminator, single enhancer 35S promoter, and TMV 5'UTR.

The p19 expression cassette in pBYR17p contains the TEV 5' UTR, as does the first expression cassette in the geminiviral replicon. This creates an inverted repeat of 131 bp. It was unknown whether the repeat would potentially cause instability due to recombination. To investigate, TEV 5'UTR was removed from the p19 cassette, by ligation of the vector fragment of pBYR17p-MRtx (containing 2 dual enhancer 35S promoters) cleaved with PvuI-AscI and a PvuI-AscI containing a fragment with the p19 cassette derived from subclone pUC-N!Tp19N, in which the TEV 5' UTR was deleted. The resulting pBYR17p2-MRtx is shown in FIG. 1G.

A vector combining the new features of pBYR17p1-MRtx (with two single enhancer 35S promoters) and pBYR17p2-MRtx (TEV 5' UTR deleted in the p19 cassette) was constructed by ligation of the vector fragment of pBYR17p1-MRtx cut with PvuI-AscI and the p19 cassette from pBYR17p2-MRtx cut with PvuI-AscI. The resulting pBYR17p3-MRtx is shown in FIG. 1H. As shown in FIG. 1H, pBYR17p3-MRtx comprises two single enhancer 35S promoters in one LIR-SIR replicon, and does not have TEV 5' UTR in the p19 cassette.

Further, a single replicon vector without the p19 cassette was constructed by ligating the vector fragment of pBYR27b cut with SbfI-SphI and the 6552 bp replicon from pBYR17p3-MRtx cut with SbfI-SphI. The resulting pBYR17b1-MRtx is shown in FIG. 1I.

In addition, a dual replicon geminiviral vector that contains the heavy chain and light chain cassettes in separate tandem replicons was constructed. One (pBYR27p2-MRtx) contains 35S promoters with double enhancers, and the other has single enhancers (pBYR27p3-MRtx). The vector fragment from pBYR17p2-MRtx digested with SacI-BsrGI was ligated to the 2264 bp fragment obtained by digestion of pBYR27p with SacI-BsrGI, containing SIR and LIR regions. The resulting pBYR27p2-MRtx is shown in FIG. 1J. As shown in FIG. 1J, pBYR27p2-MRtx comprises two LIR-SIR replicons, each contains a dual enhancer 35S, whereas the p19 cassette does not have TEV 5' UTR.

To construct pBYR27p3-MRtx (FIG. 1K), four fragments were ligated together: 1) vector pBYR17p3-MRtx cut with AscI-XhoI; 2) the AscI-XbaI fragment from pBY-HL(6D8).R containing LIR, single-enhancer 35S promoter, and TEV 5' UTR; 3) the XbaI-PstI fragment from pBYR27p2-MRtx containing the H chain cds, Ext terminator, SIR, LIR, and single-enhance 35S promoter; and 4) the PstI-XhoI fragment from pBY-HL(6D8).R containing the single enhancer 35S promoter. As shown in FIG. 1K, pBYR27p3-MRtx comprises two LIR-SIR replicons, each contains a single enhancer 35S, and the p19 cassette does not have TEV 5' UTR.

A vector pBYR27p3-MRtxKG was constructed with the backbone of pBYR27p3 but with the positions of the Rituximab H and L chain coding sequences switched (FIG. 1L). The Rituximab H chain was PCR amplified from template pBYR17p3-MRtx using primers BAA-Bsr-F (5'-CCTGTACAACAATGGCTAACAAACATCTTTCTTTG; SEQ ID NO. 7) and RituxG-Kpn-R (5'-GCGGTACCTTACTTACCAGGTGAAAGAGAC; SEQ ID NO. 9), digested the product with BsrGI-KpnI, and ligated it with pBYR27p3-MRtx digested likewise, to make pBYR27p3-MRtxG1. We PCR amplified the Rituximab L chain with primers BAA-Xba-F (5'-CCTCTAGAACAATGGCTAACAAACATCTTTCTTTG; SEQ ID NO. 5) and RituxK-Sac-R (5'-CCGAGCTCTTAGCACTCTCCCCTATTAAAAG; SEQ ID NO. 10), digested the product with XbaI-SacI, and ligated it with pBYR27p3-MRtxG1 digested likewise, to yield pBYR27p3-MRtxKG (FIG. 1L). As shown in FIG. 1L, pBYR27p3-MRtxKG comprises two LIR-SIR replicons, each contains a single enhancer 35S, and the p19 cassette does not have TEV 5' UTR.

pBYR27p3-MRtx of FIG. 1K was modified to remove a large segment of the viral C1/C2 gene by digestion with BamHI and religation of the vector fragment, to produce pBY27p3-MRtx (FIG. 1M).

A vector pBYR9-MRtxG (FIG. 2A) was constructed, comprising a single geminiviral replicon with an expression cassette for Rituximab H chain driven by the 35S promoter (duplicated enhancer), the TMV 5'UTR, and the tobacco extensin 3' terminator region (Genbank accession D13951). The vector backbone was altered to remove unnecessary components, essentially as described in Xiang et al, 1999, *Plant Mol. Biol.* 40:711-717), except that the colE1 origin of replication was inserted to increase plasmid copy number in *E. coli*, which facilitates cloning. The replicon from pBY-L(6D8) (Huang et al., 2010) was inserted via digestion and ligation at AscI-FseI restriction sites. The Rituximab H gene with extensin 3' terminator from was inserted by digestion and ligation at XbaI-EcoRI sites. The p19 expression cassette with TEV 5'UTR from pBYR17p-MRtx was inserted by digestion and ligation at PvuI-AscI sites, thus giving pBYR9-MRtxG of FIG. 2A.

A vector pBYR9-MRtxK (FIG. 2B) was constructed, comprising a single geminiviral replicon with an expression cassette for Rituximab L chain driven by the 35S promoter (duplicated enhancer), the TMV 5'UTR, and the tobacco extensin 3' terminator region. The Rituximab L gene from pBYR27p3-MRtxKG (FIG. 1L) was inserted into pBYR9-MRtxG (FIG. 2A) by digestion and ligation at XbaI-SacI sites, to give pBYR9-MRtxK of FIG. 2B.

pBYR9-MRtxG of FIG. 2A and pBYR9-MRtxK of FIG. 2B were further modified to remove one enhancer from the 35S promoter by digestion with MfeI and religation of the vector fragments to produce pBYR9a-MRtG and pBYR9a-MRtxK, respectively. These plasmids were used to construct a dual replicon single vector comprising both Rituximab H and L genes. To make the single vector having dual replicon, three fragments were ligated: 1) pBYR9a-MRtxK digested AscI-XhoI to obtain the vector fragment, 2) pBYR9a-MRtxG digested AscI-SacI to obtain the 2310 bp fragment with LIR, 35S promoter, TMV 5'UTR, and H gene, and 3) pBYR27p3-MRtx digested SacI-XhoI to obtain the 1866 bp fragment with the extensin 3' terminator, SIR, LIR, and 35S promoter. The resulting recombinant was named pBYR29a-MRtx (FIG. 2E).

pBYR9-MRtxG and pBYR9-MRtxK were also modified to remove a large segment of the viral C1/C2 gene by digestion with BamHI and religation of the vector fragments, to produce pBY9-MRtxG (FIG. 2C) and pBY9-MRtxK (FIG. 2D), respectively.

Expression vectors for BeYDV Rep and RepA proteins were constructed, in order to vary the relative amounts of Rep and RepA produced in plant cells and evaluate the effects of the resulting different conditions on expression of Rituximab. Vectors for expression of Rep without RepA used a spliced version of the C1/C2 gene in pBY037 (Mor et al., *Biotechnol. Bioeng.* 81: 430-437, 2003). The delta-intron C1:C2 gene was incorporated into an expression vector that is driven by the 35S promoter with duplicated enhancer (Huang et al., 2009). The single enhancer 35S promoter was created by deletion of the MfeI fragment, to produce pDRep109. The 35S promoter in pDRep109 was replaced by the potato ubi3 promoter with its ubiquitin coding sequence (Genbank accession L22576; Garbarino & Belknap, 1994, *Plant Mol. Biol.* 24, 119-127) by digestion and ligation with SbfI-NcoI, to make pDRep106. The ubiquitin coding sequence was removed from the ubi3 promoter segment by digesting it with_BseRI followed by blunting with T4 DNA polymerase, and then digesting with PstI; the resulting ubi3 promoter fragment was ligated with pDRep109 digested with XhoI followed by blunting with Klenow fragment of *E. coli* DNA polymerase, and then digesting with SbfI, thus yielding pDRep107. The 35S promoter in pDRep109 was replaced by the soybean vspB promoter (Mason et al., 1993, *Plant Cell* 5:241-251) by digestion and ligation with HindIII-NcoI, to make pDRep108. The nopaline synthase (NOS) promoter and 3' terminator were incorporated into a Rep expression vector named pDRep111 by ligation of 3 fragments: 1) pBI101 (Jefferson, 1997, *Plant Mol Biol Rep* 5:387-405) digested HindIII-SacI to obtain the vector fragment, 2) pBI101 digested HindIII-NcoI to obtain the 631 bp fragment with the NOS promoter, and 3) pBY037 digested NcoI-SacI to obtain the Rep coding sequence.

Vectors for expression of RepA without Rep were constructed by PCR amplification of the BeYDV C1 gene from template pRep110 (Huang et al., 2009) using primers TEV (5'-CAAGCATTCTACTTCTATTGCAGC; SEQ ID NO. 11) and RepA-Sac-R (5'-CGGAGCTCTATGTTAATTGCTTCCACAATGGGAC; SEQ ID NO. 12). The resulting DNA product was digested with BspDI-SacI and the 289 bp fragment containing the 3' end of RepA coding sequence was ligated with pDRep110 digested BspDI-SacI, to make pRepA110. A p19 expression cassette containing the potato pinII 3' terminator region (An et al., 1989, *Plant Cell* 1(1):115-22) was inserted into pRep110 via digestion and ligation at PvuI-SbfI, to make pRepA110p.

All above mentioned constructs are compared in the following Table 1, specifying the difference in the structure of p19 expressing cassette, the number of replicon and the enhancer structure of the 35s promoter in respective construct.

All T-DNA vectors were mobilized into *Agrobacterium tumefaciens* GV3101 by electroporation. The plasmids in recombinant clones were verified by restriction digestion.

TABLE 1

Constructs and their comparison

| | P19 | | Single Replicon (LIR-SIR) | | Two Replicons (LIR-SIR)-(LIR-SIR) | | 35S enhancer | | C2/C1 expression cassette contained |
|---|---|---|---|---|---|---|---|---|---|
| | | | Cassette | Cassette | Cassette | Cassette | | | |
| | +TEV | −TEV | 1 | 2 | 1 | 2 | Single | Dual | in replicon |
| pBYR27b (FIG. 1A) | — | | | | TEV 5'-Ext 3' | TMV 5'-rbcS 3' | | + | + |
| pBYR27p (FIG. 1B) | + | | | | TEV 5'-Ext 3' | TMV 5'-rbcS 3' | | + | + |
| pBYR17p (FIG. 1C) | + | | TEV 5'-Ext 3' | TMV 5'-rbcS 3' | | | | + | + |
| pBYR17p-MRtxG (FIG. 1D) | + | | TEV 5'-RtxG-Ext 3' | TMV 5'-rbcS 3' | | | | + | + |
| pBYR17p-MRtx (FIG. 1E) | + | | TEV 5'-RtxG-Ext 3' | TMV 5'-RtxK-rbcS 3' | | | | + | + |
| pBYR17p1-MRtx (FIG. 1F) | + | | TEV 5'-RtxG-Ext 3' | TMV 5'-RtxK-rbcS 3' | | | + | | + |
| pBYR17p2-MRtx (FIG. 1G) | | + | TEV 5'-RtxG-Ext 3' | TMV 5'-RtxK-rbcS 3' | | | | + | + |
| pBYR17p3-MRtx (FIG. 1H) | | + | TEV 5'-RtxG-Ext 3' | TMV 5'-RtxK-rbcS 3' | | | + | | + |
| pBYR17b1-MRtx (FIG. 1I) | — | | TEV 5'-RtxG-Ext 3' | TMV 5'-RtxK-rbcS 3' | | | + | | + |
| pBYR27p2-MRtx (FIG. 1J) | | + | | | TEV 5'-RtxG-Ext 3' | TMV 5'-RtxK-rbcS 3' | | + | + |
| pBYR27p3-MRtx (FIG. 1K) | | + | | | TEV 5'-RtxG-Ext 3' | TMV 5'-RtxK-rbcS 3' | + | | + |
| pBYR27p3-MRtxKG (FIG. 1L) | | + | | | TEV 5'-RtxK-Ext 3' | TMV 5'-RtxG-rbcS 3' | + | | + |
| pBYR9-MRtxG (FIG. 2A) | + | | TMVS'-RtxG-Ext 3' | | | | | + | + |
| pBYR9-MRtxK (FIG. 2B) | + | | TMVS'-RtxK-Ext 3' | | | | | + | + |
| pBY9-MRtxG (FIG. 2C) | + | | TMVS'-RtxG-Ext 3' | | | | | + | |
| pBY9-MRtxK (FIG. 2D) | + | | TMVS'-RtxK-Ext 3' | | | | | + | |
| pBYR29a-MRtx (FIG. 2E) | | + | | | TMVS'-RtxG-Ext 3' | TMVS'-RtxK-Ext 3' | + | | + |
| pBY27p3-MRtx (FIG. 1M) | | + | | | TEV 5'-RtxG-Ext 3' | TMV 5'-RtxK-rbcS 3' | + | | |

Example 2: Plant Inoculation and Tissue Harvest

*N. benthamiana* plants were grown in a greenhouse until 4-5 weeks old, watered with solution containing Jack's Professional Fertilizer 1.48 g/L (Hummert International 07-5925-1), then transferred to a growth chamber with fluorescent and incandescent lighting for 5 days before inoculation with *A. tumefaciens* GV3101 harboring specific T-DNA vectors. Leaves were infiltrated by the syringe method as described (Huang et al., 2009, 2010). The bacterial cells were suspended in 10 mM MES (2-N-morpholino ethanesulfonic acid), 10 mM $MgSO_4$, pH 5.5, at optical density at 600 nm ($OD_{600}$) that varied according to each experiment. In single vector experiments, the cell density was adjusted to $OD_{600}$=0.2. In experiments that used combinations of different vectors, each agrobacterial culture was adjusted to $OD_{600}$=0.2, such that with two vectors the total $OD_{600}$=0.4, and with three vectors the total $OD_{600}$=0.6. On each leaf, two different treatments were directly compared by infiltrating a different construct, or combination of different constructs, on either side of the leaf. On various days post-inoculation, infiltrated leaf tissues were harvested, weighed, quick-frozen in liquid $N_2$ and stored at −80° C. until extraction.

Leaf tissues were extracted by homogenization in extraction buffer [phosphate buffered saline (PBS), pH 7.4, 50 mM sodium ascorbate, 1 mM EDTA, 0.1% Triton X100, 2 mM PMSF, 1 µg/ml leupeptin, using 0.5 ml buffer per 0.1 g leaf sample. Homogenization was accomplished using a bead beater (Bullet Blender, Next Advance Inc., Averill Park, N.Y.) using 10 zirconium beads in a 2 ml tube, at speed setting 9 for 10 minutes at 4° C. The extracts were cleared by centrifugation at 10,000 g for 15 min at 4° C. and supernatant collected for assay. Total protein in the extract was measured by the Bradford assay using BioRad Bradford reagent and BSA as the reference standard.

IgG was then assayed using ELISA. The ELISA protocol for human IgG follows:

1) Coat ELISA plate (ThermoFisher 07-200-35, Thermo Fisher Scientific, Waltham, Mass.) with 100 µl/well goat anti-human IgG (SouthernBiotech 2040-01, Birmingham, Ala.) diluted in PBS 1:1000, incubate overnight at 4° C.;

2) Wash plate 3 times with PBS+0.5% Tween-20 (PBST);

3) Add 300 µl/well 2% BSA in PBST to block at 37° C. for 1 hour;

4) Add samples and standards, in duplicate, at 100 µl/well. Dilute with 0.1% BSA in PBST; the reference standard is human IgG 1 mg/ml (SouthernBiotech 0150-01) diluted to 100 ng/ml then serially diluted to 100, 50, 25, 12.5, 6.25, 3.125, and 1.563 ng/ml; dilute samples (extracted supernatant) at 1:100, 1:500, 1:2500, and 1:12500; incubate the samples and standards for 1 hour at 37° C.;

5) Wash plate 3 times with PBST;

6) Probe wells with 100 µl/well goat anti-human kappa-HRP conjugate (SouthernBiotech 2060-05) diluted 1:4000 with 0.5% BSA in PBST. Incubate 1 hour at 37° C.

7) Wash plate 3× in PBST;

8) Develop with SureBlue TMB 1-component Microwell Peroxidase Substrate (KPL 52-00-01, KPL, Inc. Gaithersburg, Md.), 100 µl/well for 4 min, and stop reaction with 100 µl/well 1N HCl; and 9) Read plate at 450 nm.

Example 3: Rituximab Expression Using Various Geminiviral Replicon Vectors

Experiment 1

In the first experiment, Rituximab expression with 7 different constructs (FIGS. 1E, 1F, 1G, 1H, 1I, 1J, and 1K, respectively) infiltrated into leaves of *N. benthamiana* and harvested after 3 days (FIG. 3) were examined. The highest expression was obtained using pBYR17p-MRtx (FIG. 1E), pBYR17b1-MRtx (FIG. 1I), and pBYR27p3-MRtx (FIG. 1K), with mean levels of 573, 515, and 578 µg/g leaf mass, respectively. There was no statistically significant difference among these values (obtained from 3 replicate samples). Interestingly, pBYR17b1-MRtx of FIG. 1I showed the highest S.D. of the mean value (388, 362, and 795 µg/g leaf mass), which suggests that lack of the p19 RNAi suppressor cassette in this construct allowed variable degree of RNAi expression silencing. The use of 35S promoters with dual enhancer (17p) or single enhancer (17p1) in the single replicon context had no significant effect. However, in vectors containing dual geminiviral replicons (27p2 and 27p3), the single enhancer promoters of pBYR27p3-MRtx yielded better results than the duplicated enhancer promoters of pBYR27p2-MRtx, despite that duplicated enhancer effect in gene expression from 35S promoter duplication was expected. For example, the duplicated enhancer 35S promoter is well known to increase transcriptional activity over the native single enhancer form (see Kay et al., 1987, *Science* 236:1299-1302). Moreover, this is surprising as the single enhancer versus double enhancer promoter did not behave this way in the single replicon format, for example, comparing 17p2 versus 17p3 (FIG. 3).

Experiment 2

In the second experiment, selected constructs were directly compared pair-wise, by infiltrating them on opposite sides of the same leaves in order to minimize leaf-to-leaf variation (FIG. 4). Comparing single replicon construct pBYR17p3-MRtx (FIG. 1H) with dual replicon construct pBYR27p3-MRtx (FIG. 1K), the latter was significantly better (mean 222 vs. 478 µg/g leaf mass), which was contrary to observations made in comparing single versus dual replicon (Huang, 2010). Comparing single replicon constructs with or without p19 (17p1MRtx (FIG. 1F) and 17b1MRtx (FIG. 1I), respectively), no significant difference was observed, although the mean level was higher for 17b1. Similarly, no significant difference occurred when comparing 17p1MRtx (FIG. 1F) and 17p3MRtx (FIG. 1H), which differ only in the presence or absence of the TEV 5' UTR in the p19 expression cassette. Overall, pBYR27p3-MRtx (FIG. 1K) gave the highest expression in both experiments.

Experiment 3

In the third experiment, expression with vectors pBYR27p3-MRtx (FIG. 1K) and pBYR27p3-MRtxKG (FIG. 1L) was compared, which differ in the linear positions of the heavy and light chain coding sequences. Since replicon size could potentially affect the efficiency of replication, all previous constructs placed the shorter light chain gene in the replicon that contains the geminiviral C1/C2 gene, thus yielding replicons of similar size for the heavy and light chain genes. Preliminary experiment with these constructs showed no significant difference in their Rituximab expression levels (data not shown).

Among 8 different constructs tested, pBYR27p3-MRtx (FIG. 1K) was selected as the best candidate to move forward.

Experiment 4

In a fourth experiment, the relative levels of expression of Rep and RepA was varied in order to evaluate the effect on Rituximab expression from a dual replicon from which C1/C2 was largely deleted. In a native BeYDV replicon, the C1/C2 RNA is transcribed from a promoter in the LIR, and Rep is expressed when the C1/C2 mRNA is spliced to remove a short intron, while RepA is produced from the C1 coding sequence when no splicing occurs. Since the splicing event is relatively rare, RepA is typically produced at substantially higher levels than Rep, a typical native viral relative expression, when without manipulation. Rep protein functions in DNA nicking and ligating activities necessary for genome replication, while RepA appears to interfere with normal cell cycle progression in order to maintain the nucleus in S phase, thus favoring DNA synthesis. Separate expression cassettes for Rep and RepA were constructed, using various promoters to achieve different rates of transcription, i.e. atypical relative expression, for Rep and RepA mRNAs. In preliminary studies that varied RepA expression while holding Rep expression constant, the expression of a reporter gene from a C1/C2-deleted replicon was the highest when RepA expression was the highest (data not shown). Thus, we used the RepA vector pRepA110p, in which RepA is driven by the 35S promoter with duplicated enhancer, and co-delivered various Rep expression constructs with pRepA110p and pBY27p3-MRtx. The Rep expression constructs used, i.e., pDRep106, pDRep107, pDRep108, and pDRep111, were expected to produce levels of Rep substantially lower than the RepA expression driven by pRepA110p. The previous best vector selected from Experiment 3, pBYR27p3-MRtx (FIG. 1K, containing C1/C2 gene expressing replicon) was compared with the Rep/RepA/pBY27p3-MRtx (pBY27p3-MRtx contains a replicon without the C1/C2 gene) combinations.

The leaf inoculation sites were harvested at 4 or 5 days post-inoculation (dpi). The data (FIG. 5) show the mean values (±SE) of Rituximab expression at 4 or 5 days. All of the Rep/RepA/pBY27p3-MRtx combinations performed better than pBYR27p3-MRtx, with the exception of the one with pDRep108 (vspB promoter). The combination that used pDRep106 (ubi3 promoter with ubiquitin fusion) performed best, at 430 μg/g leaf mass, compared with pBYR27p3-MRtx at 275 μg/g leaf mass. Although previous experiments showed higher expression of pBYR27p3-MRtx in number, comparisons are most accurate when the treatments are performed in the same experiment, due to the variability of plants in different experiments. Thus far, the results show that Rituximab expression can be improved using a combination of vectors to provide expression of Rep and RepA and a C1/C2-deleted dual replicon vector for expression of Rituximab H and L chains.

Experiment 5

In a fifth experiment, pBYR27p3-MRtx (FIG. 1K) was compared with a combination of separate BeYDV replicon vectors for the Rituximab H and L chains. For the combination treatment, pBYR9-MRtxG (FIG. 2A) and pBYR9-MRtxK (FIG. 2B) were used, which provide each replicon on a separate vector. Both expression cassettes in pBYR9-MRtxG and pBYR9-MRtxK used the 35S promoter with duplicated enhancer, TMV 5'UTR, and extensin 3' terminator. By comparison, pBYR27p3-MRtx, for each cassette, used the 35S promoter with single enhancer, and either TEV 5'UTR/Ext 3' terminator or TMV 5'UTR/rbcS 3' terminator (Table 1). The data (FIG. 6) clearly show a substantial benefit of the combination treatment (pBYR9-MRtxG+pBYR9-MRtxK) over pBYR27p3-MRtx. A mean expression value of 1115 μg/g leaf tissue (n=6) by the combination treatment versus 297 μg/g leaf tissue (n=6) by dual replicon in a single vector were observed (FIG. 6A). The dramatic improvement in the level of expression was observed and further confirmed when expression is calculated on the basis of total soluble protein (TSP, FIG. 6B). Such high level of benefit was unexpected, because the 5' UTRs and 3' terminators in pBYR27p3-MRtx had been deliberately designed to be different, in order to minimize the amount of sequence duplication in the H and L mRNAs. It was thought that less sequence duplication would decrease the potential for generation of siRNA and result in less RNAi gene silencing; however, the data appear to contradict this hypothesis.

In the experiment 5 described above, both treatments were inoculated in combination with pRepA110p, in order to examine the effect of over-expression of RepA, which was shown to be beneficial in the experiment 4 of FIG. 5. In this case, the extra RepA treatments decreased Rituximab expression somewhat (FIG. 6). Nonetheless, the benefit of (pBYR9-MRtxG+pBYR9-MRtxK) over pBYR27p3-MRtx was maintained at 2-3 fold, close to that in treatments without pRepA110p. Thus, the improvement observed with the combinations used in the experiment of FIG. 5 (Experiment 4) may be a function of both the ratio of Rep/RepA expression and the total amount of RepA. In the combination (pBYR9-MRtxG+pBYR9-MRtxK) used in the experiment 5 of FIG. 6, both vectors contain the C1/C2 gene in its native position in the replicon, which may provide a Rep/RepA ratio and total RepA at optimal values. It will be of interest to examine combinations including the C1/C2-deleted replicon constructs pBY9-MRtxG (FIG. 2C) and pBY9-MRtxK (FIG. 2D) co-delivered with pDRep106+pRepA110p, in order to evaluate this hypothesis.

Experiment 6

In this experiment, a dual replicon single vector system was examined, pBYR29a-MRtx (FIG. 2E), which used 35S promoters with single enhancers, TMV 5'UTRs, and extensin 3' terminators for both Rituximab H and L genes. The dual replicon vector pBYR29a-MRtx was compared to the combination of single replicon vectors pBYR9-MRtxG (FIG. 2A) and pBYR9-MRtxK (FIG. 2B). In the single replicon vectors, the H and L chain genes were transcribed by 35S promoters with dual enhancers, while the dual replicon vector pBYR29a-MRtx used the single enhancer 35S promoters. Expression of Rituximab was found to be very similar with the two systems: 1404±205 (S.D.) μg/g leaf mass (n=2) for pBYR29a-MRtx and 1727±806 (S.D.) μg/g leaf mass (n=2) for the combination. On the basis of total soluble protein, the expression values were the same for both treatments, 66±18 (S.D.) μg/mg TSP. It is unclear why the combination of vectors with dual enhancer 35S promoters did not perform better than the single vector dual replicon system that used single enhancer 35S promoters.

Without being bound by the theory, through our comparative experiments, other features that may have dramatically enhanced the protein expression in both the single vector pBYR29a-MRtx and combination vector treatment seem to include: 1) the use of the TMV 5'UTR instead of TEV 5'UTR for both the H and L chain genes, and 2) the use of the extensin 3' terminator instead of rbcS 3' terminator for both the H and L chain genes.

What is claimed is:

1. A vector comprising a long intergenic region (LIR) of a geminivirus genome, followed by two nucleic acid segments followed by a short intergenic region (SIR) of a geminivirus genome, followed by one or more nucleic acids encoding Rep and RepA proteins of a geminivirus genome, followed by a LIR, wherein the two nucleic acid segments comprise:
   (a) a nucleic acid segment comprising at least one promoter, a 5'UTR, a region encoding a heavy chain of Ritixumab, and a 3' terminator; and
   (b) a nucleic acid segment comprising at least one promoter, a 5'UTR, a region encoding a light chain of Ritixumab, and a 3' terminator;

wherein the two nucleic acid segments comprise a single replicon.

2. The vector of claim 1, further comprising a nucleic acid segment that comprises a gene-silencing inhibitor.

3. The vector of claim 1, wherein the 5'UTR of the first and second nucleic acid segment comprise the same sequence and the 3' terminator of the first and second nucleic acid segment comprise the same sequence.

4. The vector of claim 1, wherein the 5'UTR of the first and second nucleic acid segment do not comprise the same sequence and the 3' terminator of the first and second nucleic acid segment do not comprise the same sequence.

5. A method of producing Rituximab in a plant cell comprising:
   (a) obtaining a vector of claim 1
   (b) introducing the vector into a plant cell; and
   (c) allowing expression of the replicon comprising the first and the second chain of Rituximab.

6. The method of claim 5, further comprising a full assembly of the first and the second chains of Rituximab.

7. The vector of claim 1, wherein the 3' terminator comprises a tobacco extensin gene terminator region.

* * * * *

SEQUENCE LISTING

<160> NUMBER OF SEQ ID NOS: 12

<210> SEQ ID NO 1
<211> LENGTH: 31
<212> TYPE: DNA
<213> ORGANISM: Artificial Sequence
<220> FEATURE:
<223> OTHER INFORMATION: Artificial sequence used as a primer

<400> SEQUENCE: 1
gtgagctcga agtgacatca caaagttgaa g 31

<210> SEQ ID NO 2
<211> LENGTH: 31
<212> TYPE: DNA
<213> ORGANISM: Artificial Sequence
<220> FEATURE:
<223> OTHER INFORMATION: Artificial sequence used as a primer

<400> SEQUENCE: 2
cagaattcgt cataactgta gaaatgattc c 31

<210> SEQ ID NO 3
<211> LENGTH: 26
<212> TYPE: DNA
<213> ORGANISM: Artificial Sequence
<220> FEATURE:
<223> OTHER INFORMATION: Artificial sequence used as a primer

<400> SEQUENCE: 3
cgatcgacac tagtaagctg gcgcgc 26

<210> SEQ ID NO 4
<211> LENGTH: 15
<212> TYPE: DNA
<213> ORGANISM: Artificial Sequence
<220> FEATURE:
<223> OTHER INFORMATION: Artificial sequence used as a primer

<400> SEQUENCE: 4
tgtacaacag gtacc 15

<210> SEQ ID NO 5
<211> LENGTH: 35
<212> TYPE: DNA
<213> ORGANISM: Artificial Sequence
<220> FEATURE:
<223> OTHER INFORMATION: Artificial sequence used as a primer

<400> SEQUENCE: 5
cctctagaac aatggctaac aaacatcttt ctttg 35

<210> SEQ ID NO 6
<211> LENGTH: 30
<212> TYPE: DNA
<213> ORGANISM: Artificial Sequence
<220> FEATURE:
<223> OTHER INFORMATION: Artificial sequence used as a primer

<400> SEQUENCE: 6
ccgagctctt acttaccagg tgaaagagac 30

<210> SEQ ID NO 7
<211> LENGTH: 35
<212> TYPE: DNA
<213> ORGANISM: Artificial Sequence
<220> FEATURE:
<223> OTHER INFORMATION: Artificial sequence used as a primer

<400> SEQUENCE: 7
cctgtacaac aatggctaac aaacatcttt ctttg 35

<210> SEQ ID NO 8
<211> LENGTH: 31
<212> TYPE: DNA
<213> ORGANISM: Artificial Sequence
<220> FEATURE:
<223> OTHER INFORMATION: Artificial sequence used as a primer

<400> SEQUENCE: 8
gcggtacctt agcactctcc cctattaaaa g 31

<210> SEQ ID NO 9
<211> LENGTH: 30
<212> TYPE: DNA
<213> ORGANISM: Artificial Sequence
<220> FEATURE:
<223> OTHER INFORMATION: Artificial sequence used as a primer

<400> SEQUENCE: 9
gcggtacctt acttaccagg tgaaagagac 30

<210> SEQ ID NO 10
<211> LENGTH: 31
<212> TYPE: DNA
<213> ORGANISM: Artificial Sequence
<220> FEATURE:
<223> OTHER INFORMATION: Artificial sequence used as a primer

<400> SEQUENCE: 10
ccgagctctt agcactctcc cctattaaaa g 31

<210> SEQ ID NO 11
<211> LENGTH: 24
<212> TYPE: DNA
<213> ORGANISM: Artificial Sequence
<220> FEATURE:
<223> OTHER INFORMATION: Artificial sequence used as a primer

<400> SEQUENCE: 11
caagcattct acttctattg cagc 24

<210> SEQ ID NO 12
<211> LENGTH: 34
<212> TYPE: DNA
<213> ORGANISM: Artificial Sequence
<220> FEATURE:
<223> OTHER INFORMATION: Artificial sequence used as a primer

<400> SEQUENCE: 12
cggagctcta tgttaattgc ttccacaatg ggac 34